(12) United States Patent
Nishina

(10) Patent No.: US 8,991,257 B2
(45) Date of Patent: Mar. 31, 2015

(54) ULTRASOUND PROBE SYSTEM

(71) Applicant: Olympus Medical Systems Corp., Tokyo (JP)

(72) Inventor: Kenichi Nishina, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/199,251

(22) Filed: Mar. 6, 2014

(65) Prior Publication Data

US 2014/0238138 A1    Aug. 28, 2014

Related U.S. Application Data

(63) Continuation of application No. PCT/JP2013/082725, filed on Dec. 5, 2013.

(30) Foreign Application Priority Data

Jan. 16, 2013    (JP) .................. 2013-005626

(51) Int. Cl.
| | | |
|---|---|---|
| *G01N 29/04* | (2006.01) | |
| *G01N 29/24* | (2006.01) | |
| *A61B 8/12* | (2006.01) | |
| *A61B 1/018* | (2006.01) | |

(52) U.S. Cl.
CPC ......... *G01N 29/24* (2013.01); *A61B 8/12* (2013.01); *G01N 29/04* (2013.01); *G01N 2291/023* (2013.01); *A61B 1/018* (2013.01)
USPC .......................................................... 73/627

(58) Field of Classification Search
USPC ............... 73/627; 600/437, 462–463
See application file for complete search history.

(56) References Cited

U.S. PATENT DOCUMENTS

| | | | |
|---|---|---|---|
| 4,794,931 A | | 1/1989 | Yock |
| 5,910,113 A | * | 6/1999 | Pruter ........................... 600/437 |
| 6,270,471 B1 | * | 8/2001 | Hechel et al. ................... 604/22 |
| 6,514,215 B1 | * | 2/2003 | Ouchi ........................... 600/564 |
| 6,689,066 B1 | * | 2/2004 | Omura et al. ................. 600/463 |
| 8,852,113 B2 | * | 10/2014 | Nishina et al. ................ 600/466 |
| 2013/0109974 A1 | | 5/2013 | Nishina et al. |

FOREIGN PATENT DOCUMENTS

| | | |
|---|---|---|
| EP | 0234951 A1 | 9/1987 |
| EP | 2 617 361 A1 | 7/2013 |

(Continued)

*Primary Examiner* — J M Saint Surin
(74) *Attorney, Agent, or Firm* — Scully, Scott, Murphy & Presser, PC

(57) ABSTRACT

An ultrasound probe system includes a main body portion, an ultrasound observation portion transmitting ultrasound in a side surface direction of the main body portion and receiving a reflected wave, a distal-end portion provided such that a proximal-end face, on a proximal-end side is adjacent to a distal-end in an axial direction of the main body portion, a sheath portion housing the main body portion inside to be capable of advancing and retracting in the axial direction, a distal-end face arranged at a distal-end of the sheath portion and facing the proximal-end face, a specimen collecting portion provided on the proximal-end face and/or the distal-end face, the specimen collecting portion being formed at an acute angle to separate a specimen from a subject, and an edge portion arranged on the proximal-end face or the distal-end face to cross the entire circumference of the specimen collecting portion to cut the specimen.

4 Claims, 20 Drawing Sheets

(56) References Cited

FOREIGN PATENT DOCUMENTS

| | | |
|---|---|---|
| JP | 62-270140 A | 11/1987 |
| JP | 2001-104316 A | 4/2001 |
| JP | 2004-216159 A | 8/2004 |
| JP | 2009-247550 A | 10/2009 |
| JP | 2010-274123 A | 12/2010 |
| JP | 5226908 B1 | 7/2013 |
| WO | WO 2012/133276 A1 | 10/2012 |
| WO | WO 2012/176543 A1 | 12/2012 |

* cited by examiner

ULTRASOUND PROBE SYSTEM

CROSS REFERENCE TO RELATED APPLICATION

This application is a continuation application of PCT/JP2013/082725 filed on Dec. 5, 2013 and claims benefit of Japanese Application No. 2013-005626 filed in Japan on Jan. 16, 2013, the entire contents of which are incorporated herein by this reference.

BACKGROUND OF THE INVENTION

1. Field of the Invention

The present invention relates to an ultrasound probe system including a sheath portion configured to house an elongated main body portion, which is provided with an ultrasound observation portion, to be movable back and forth in an insertion axial direction.

2. Description of the Related Art

Japanese Patent Application Laid-Open Publication No. 2004-216159 discloses a method and a configuration of an ultrasound probe system for inserting a sheath into a lumen together with an ultrasound probe in a state in which the ultrasound probe is inserted into the sheath and, after performing ultrasound observation of an examined region in the lumen using an ultrasound observation portion provided at a distal end in an axial direction of the ultrasound probe, pulling out the ultrasound probe from the sheath and, thereafter, inserting the specimen collecting tool into the sheath to collect a specimen, which is a living tissue of the examined region.

SUMMARY OF THE INVENTION

An ultrasound probe system according to an aspect of the present invention includes: a bar-like main body portion; an ultrasound observation portion provided in the main body portion and configured to transmit ultrasound in a side surface direction of the main body portion and receive a reflected wave; a distal end portion provided such that a proximal end face, which is a surface on a proximal end side, is adjacent to a distal end in an axial direction of the main body portion, the distal end portion having a diameter larger than the main body portion; a cylindrical sheath portion having a diameter larger than the main body portion and configured to house the main body portion on an inside thereof to be capable of advancing and retracting in the axial direction; a distal end face arranged at a distal end of the sheath portion and facing the proximal end face; a specimen collecting portion provided on at least one of the proximal end face and the distal end face, an entire circumference of the specimen collecting portion being formed at an acute angle toward the axial direction in order to separate a specimen from a subject in an annular shape; and an edge portion arranged on the proximal end face or the distal end face to cross the entire circumference of the specimen collecting portion in order to cut the annular specimen collected by the specimen collecting portion.

DETAILED DESCRIPTION OF THE PREFERRED EMBODIMENTS

Embodiments of the present invention are explained below with reference to the drawings.

(First Embodiment)

Figure 1:
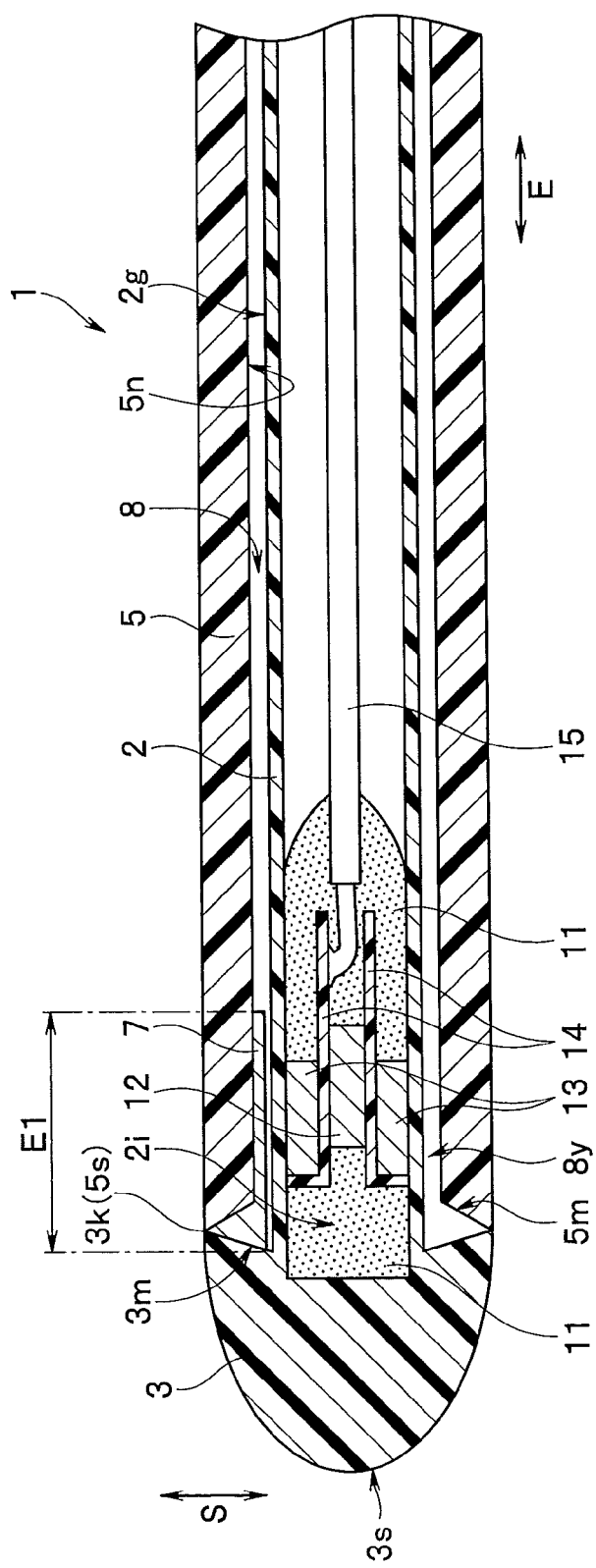
FIG. 1 is a partial sectional view showing, in a closed state of a specimen collection port, a distal end side in an axial direction of an ultrasound probe system in a first embodiment.
Figure 2:
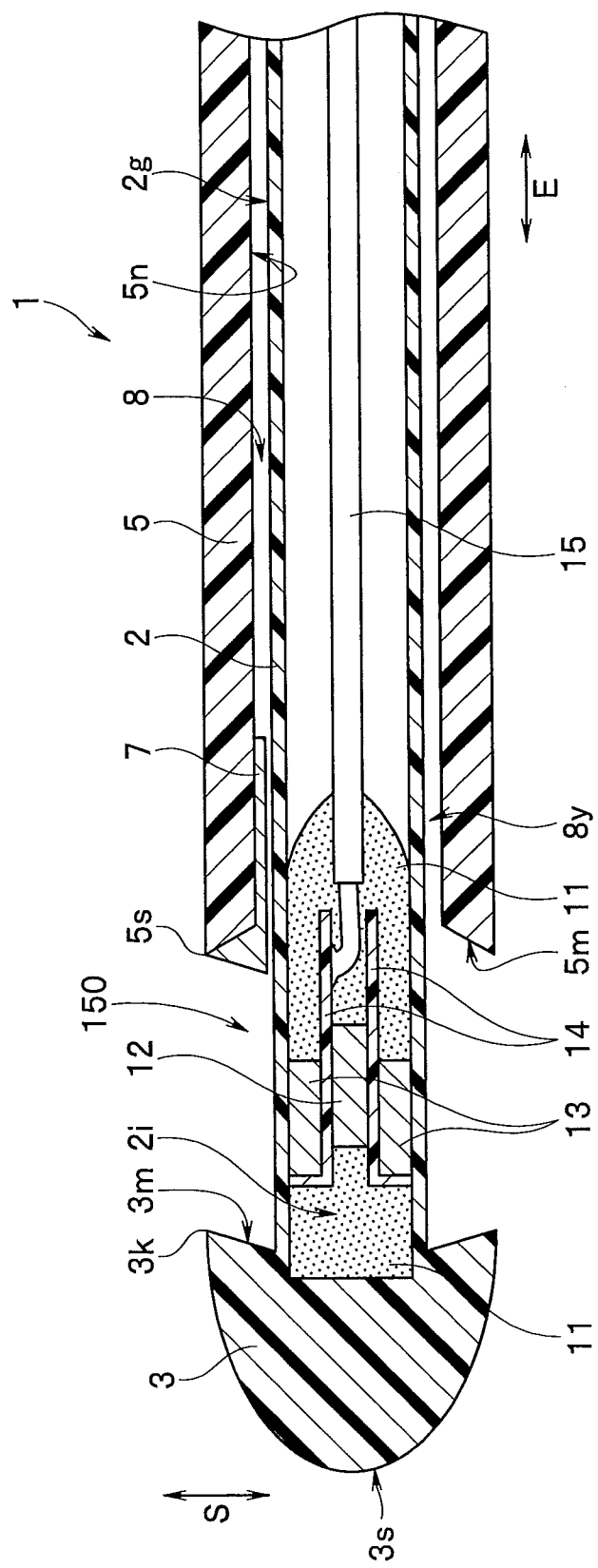
FIG. 2 is a partial sectional view showing the distal end side in the axial direction of the ultrasound probe system in an open state of the specimen collection port shown in FIG. 1.

FIG. 1 is a partial sectional view showing, in a closed state of a specimen collection port, a distal end side in an axial direction of an ultrasound probe system in the present embodiment. FIG. 2 is a partial sectional view showing the distal end side in the axial direction of the ultrasound probe system in an open state of the specimen collection port shown in FIG. 1.

Figure 3:
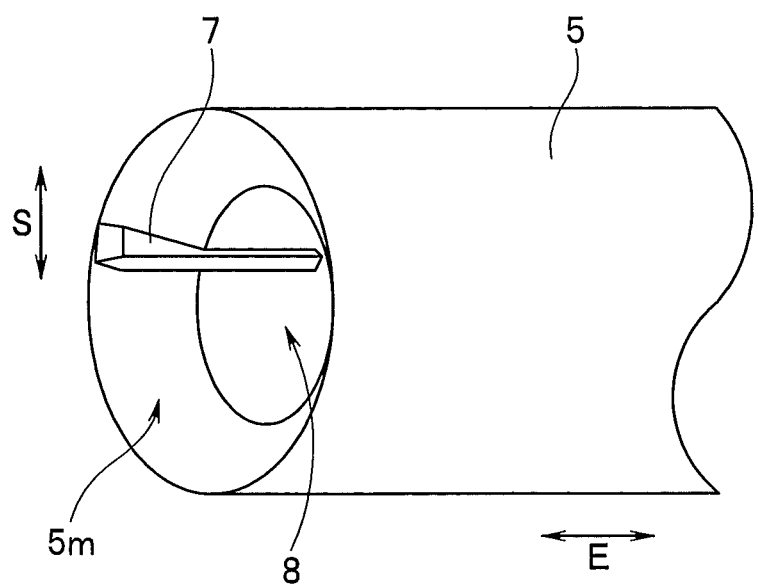
FIG. 3 is a perspective view showing a distal end side in the axial direction of a sheath portion shown in FIG. 1 together with an edge portion in enlargement.
Figure 4:
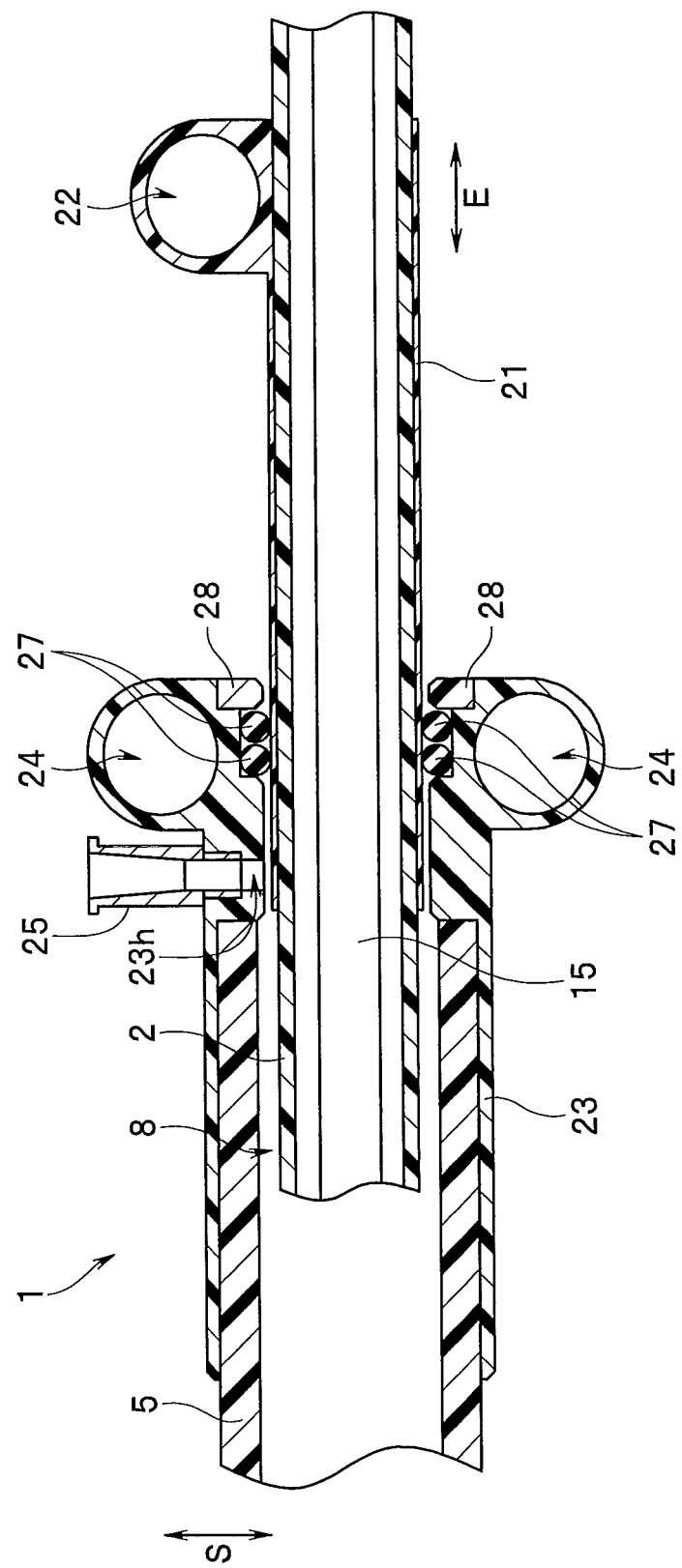
FIG. 4 is a partial sectional view showing positions in the axial direction in the closed state of the specimen collection port shown in FIG. 1 in respective operation members of the sheath portion and a main body portion provided in a halfway position in the axial direction of the ultrasound probe system shown in FIG. 1.
Figure 5:
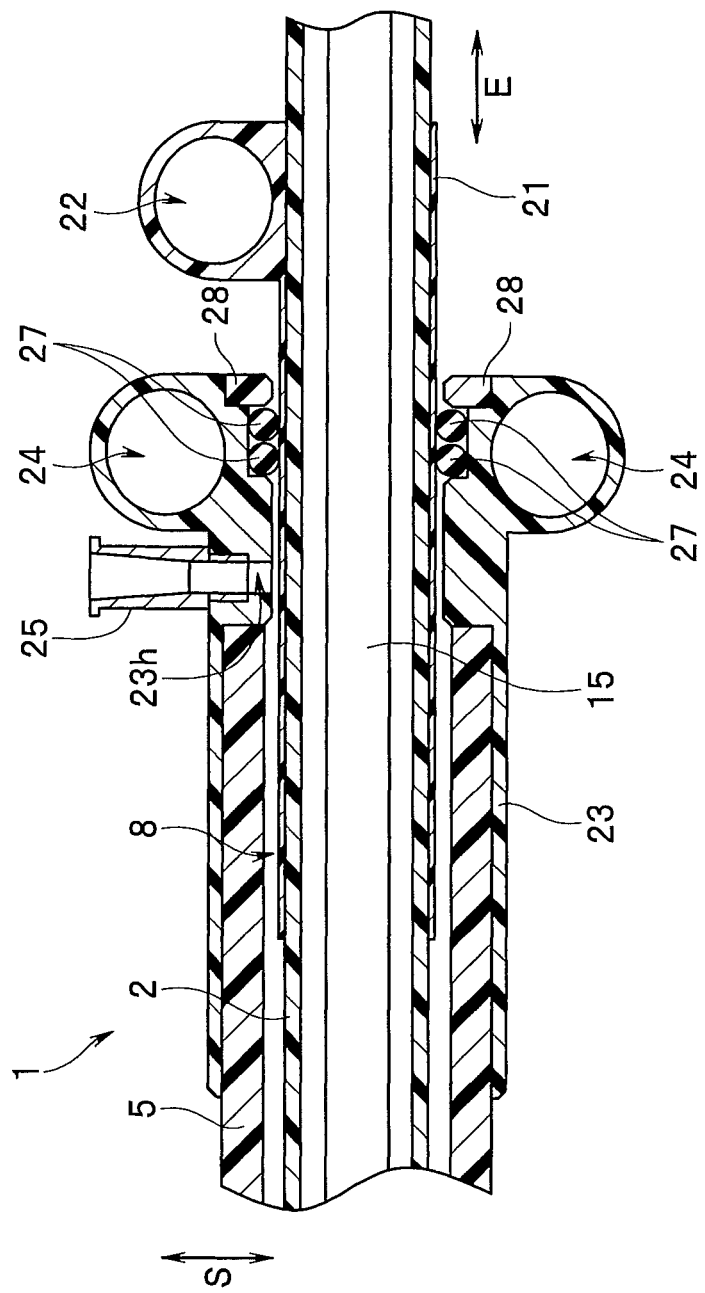
FIG. 5 is a partial sectional view showing positions in the axial direction in the open state of the specimen collection port shown in FIG. 2 in the respective operation members of the sheath portion and the main body portion shown in FIG. 4.

FIG. 3 is a perspective view showing a distal end side in the axial direction of a sheath portion shown in FIG. 1 together with an edge portion in enlargement. FIG. 4 is a partial sectional view showing positions in the axial direction in the closed state of the specimen collection port shown in FIG. 1 in respective operation members of the sheath portion and a main body portion provided in a halfway position in the axial direction of the ultrasound probe system shown in FIG. 1. FIG. 5 is a partial sectional view showing positions in the axial direction in the open state of the specimen collection port shown in FIG. 2 in the respective operation members of the sheath portion and the main body portion shown in FIG. 4.

Figure 6:
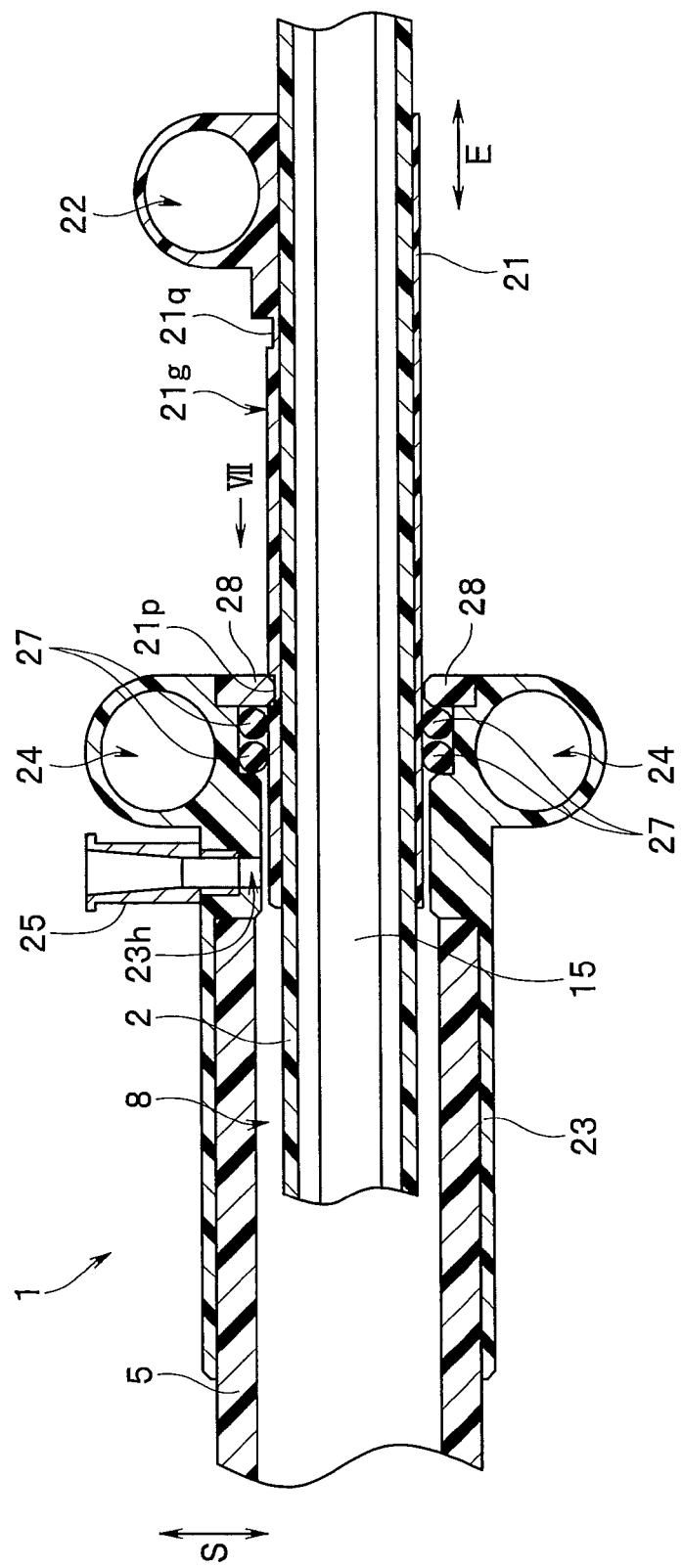
FIG. 6 is a partial sectional view showing a state in which the positions in the axial direction of the respective operation members of the sheath portion and the main body portion shown in FIG. 5 are fixed in the closed state of the specimen collection port shown in FIG. 2.
Figure 7:
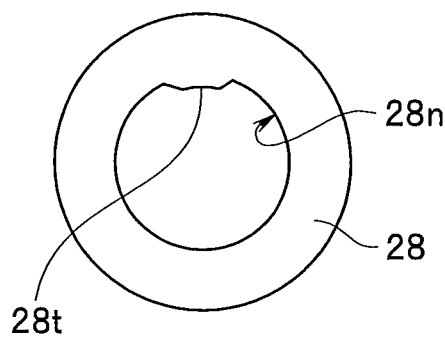
FIG. 7 is a plan view of an O-shaped ring stop member viewed from a VII direction in FIG. 6.

Further, FIG. 6 is a partial sectional view showing a state in which the positions in the axial direction of the respective operation members of the sheath portion and the main body portion shown in FIG. 5 are fixed in the closed state of the specimen collection port shown in FIG. 2. FIG. 7 is a plan view of an O-shaped ring stop member viewed from a VII direction in FIG. 6.

As shown in FIG. 1 and FIG. 2, an ultrasound probe system 1 is, for example, inserted through a not-shown treatment instrument insert-through channel formed in an insertion portion 122a of an endoscope 122 (see FIG. 20 for both of the insertion portion 122a and the endoscope 122) or independently inserted into a subject. The ultrasound probe system 1 includes a bar-like, that is, elongated tubular main body portion 2 inserted into the subject via the treatment instrument insert-through channel or directly.

Note that the main body portion 2 may be rigid or may be deformable and, for example, may be formed of a material having elasticity. Specific examples of the material having elasticity include polyamide resin. The main body portion 2 is formed of a material having higher stretchability in an axial direction E of the main body portion 2 than a below-mentioned sheath portion 5.

On a distal end side in the axial direction E in an inside 2i of the main body portion 2, an ultrasound observation portion 13 that transmits ultrasound in a side surface direction S crossing the axial direction E of the main body portion 2 to thereby obtain an ultrasound image in a subject is provided.

The ultrasound observation portion 13 is configured from a ring-like ultrasound transducer. The ultrasound observation portion 13 is fixed to the distal end side in the axial direction E on the inside 2i of the main body portion 2 by an adhesive 11 and fixed to a substrate 14 on which an IC 12 is mounted.

On the inside 2i of the main body portion 2, an ultrasound transducer cable 15 is extended to a back in the axial direction E from the substrate 14. An extending end of the ultrasound transducer cable 15 is electrically connected to an electric connector 51 in a below-mentioned connector 40 (see FIG. 14 for both of the electric connector 51 and the connector 40) fixed to a proximal end in the axial direction E of the main body portion 2. The ultrasound transducer cable 15 is a cable for transmitting, to the ultrasound observation portion 13, an electric pulse signal outputted from an ultrasound observation device 123 (see FIG. 20) to which the electric connector 51 is connected.

A distal end portion 3 having a diameter larger than the main body portion 2 is provided at a distal end in the axial direction E of the main body portion 2. In the distal end portion 3, a proximal end face 3m is formed as an inclined surface inclined further backward in the axial direction E toward an outer side in a radial direction from a part on an inner side having substantially a same diameter as an outer circumferential surface 2g at the distal end in the axial direction E of the main body portion 2.

Therefore, in the distal end portion 3, a proximal end 3k in the axial direction E, which is an outer circumference end portion of the proximal end face 3m, is formed at an acute angle by an outer circumferential surface on a proximal end side in the axial direction E of the distal end portion 3 and the proximal end face 3m. That is, the proximal end 3k is formed as an acute edge portion.

The proximal end 3k functions as a specimen collecting portion configured to collect a specimen in an examined region in the subject. Note that the specimen collecting portion may be separated from the proximal end 3k. The specimen collecting portion may be fixed to the proximal end 3k by bonding or insert molding.

A distal end face 3s at a distal end in the axial direction of the distal end portion 3 is formed as, for example, a curved surface. In FIG. 1, the distal end portion 3 has a substantially bullet-like shape in section. In the present embodiment, the distal end portion 3 is formed integrally with the main body portion 2.

An outer circumference of the main body portion 2 is covered with, along the axial direction E, the sheath portion 5 having a diameter larger than the main body portion 2 and having an outer diameter substantially the same as an outer diameter on the proximal end side in the axial direction E of the distal end portion 3. Note that the sheath portion 5 is inserted into the subject having a plurality of curved portions. Therefore, in order to secure insertability, the sheath portion 5 is formed of resin having flexibility and having biocompatibility. Note that examples of the resin forming the sheath portion 5 include polyethylene, fluorocarbon resin, and PEEK. On a distal end side in the axial direction E of the sheath portion 5, a part opposed to the ultrasound observation portion 13 has ultrasound permeability.

The sheath portion 5 houses the main body portion 2 on an inside to be movable back and forth in the axial direction E. As shown in FIG. 1 to FIG. 3, a distal end face 5m at a distal end in the axial direction E as an inclined surface further inclined backward in the axial direction E toward an inner side in a radial direction from an outer circumferential surface of the sheath portion 5.

Therefore, in the sheath portion 5, a distal end 5s in the axial direction E, which is an outer circumference end portion of the distal end face 5m, is formed at an acute angle by an outer circumferential surface on the distal end side in the axial direction E of the sheath portion 5 and the distal end face 5m. That is, the distal end 5s is formed as an acute edge portion.

The distal end 5s functions as a specimen collecting portion configured to collect a specimen in an examined region in the subject. Note that the specimen collecting portion may be separate from the distal end 5s. Only the specimen collecting portion may be fixed to the distal end 5s by bonding or insert molding.

Note that, as explained above, the specimen collecting portion is the proximal end 3k of the distal end portion 3 and the distal end 5s of the sheath portion 5 or being provided at the proximal end 3k and the distal end 5s. However, the specimen collecting portion may be any one of the proximal end 3k and the distal end 5s itself or may be provided at any one of the proximal end 3k and the distal end 5s.

The sheath portion 5 is slid, whereby the distal end 5s of the sheath portion 5 comes into contact with the proximal end 3k of the distal end portion 3 as shown in FIG. 1. In this state, a below-mentioned specimen collection port 150 (see FIG. 2) changes to a closed state.

When the main body portion 2 is moved further forward in the axial direction E than the sheath portion 5 from a position where the distal end 5s shown in FIG. 1 comes into contact with the proximal end 3k of the distal end portion 3 or when the sheath portion 5 is moved further backward in the axial direction E than the main body portion 2, as shown in FIG. 2, the proximal end 3k separates from the distal end 5s in the axial direction E. At this point, as shown in FIG. 2, the specimen collection port 150 is opened between the proximal end 3k and the distal end 5s.

The specimen collection port 150 is an introduction port for, when the ultrasound probe system 1 is inserted into a narrow portion 81k (see FIG. 8) of a lumen (e.g., pulmonary periphery bronchi) 81 due to a lesion part 85, which is an examined region in the subject, and the specimen collection port 150 changes to an open state in which the proximal end 3k separates from the distal end 5s in the axial direction E as shown in FIG. 2, introducing a specimen of the lesion part 85 in the narrow portion 81k to a vicinity of the outer circumferential surface 2g of the main body portion 2 in the sheath portion 5.

Note that, in a state in which the specimen is introduced to the vicinity of the outer circumferential surface 2g of the main body portion 2 via the specimen collection port 150, as shown in FIG. 1, the main body portion 2 is moved backward in the axial direction E or the sheath portion 5 is moved forward in the axial direction E to a position where the specimen collection port 150 changes to the closed state in which the distal end 5s comes into contact with the proximal end 3k, whereby the specimen is sandwiched by the distal end 5s and the proximal end 3k. A part of the specimen is cut by at least one of the distal end 5s and the proximal end 3k.

As explained above, since the sheath portion 5 is formed in a diameter larger than the main body portion 2, a space 8 is formed between an inner circumferential surface 5n of the sheath portion 5 and the outer circumferential surface 2g of the main body portion 2. Note that in the space 8, for example, saline functioning as an ultrasound transmission medium is filled from a below-mentioned pipe sleeve 25 (see FIG. 4).

As shown in FIG. 2, in the open state of the specimen collection port 150, the saline leaks from the space 8. However, instead, mucus or the like in the subject enters the space 8, whereby the entered liquid functions as the ultrasound transmission medium.

Note that, when an interval in a radial direction in the space 8 is narrow, that is, when an interval between the outer circumferential surface 2g of the main body portion 2 and the inner circumferential surface 5n of the sheath portion 5 in the radial direction is narrow, outside the subject, in the open state of the specimen collection port 150 shown in FIG. 2, the saline may be injected from the specimen collection port 150 into the space 8 using a capillary phenomenon. The capillary phenomenon tends to occur when hydrophilic treatment is applied to the outer circumferential surface 2g of the main body portion 2 and the inner circumferential surface 5n of the sheath portion 5.

Further, on a distal end side in the axial direction E of the space 8, a housing portion 8y is provided that has a predetermined length from the distal end 5s of the sheath portion 5 along the axial direction E and in which a specimen collected by at least one of the proximal end 3y and the distal end 5s is housed.

Note that a part of the outer circumferential surface 2g of the main body portion 2 facing the housing portion 8y may be subjected to surface treatment to have higher hydrophobicity than the other parts on the outer circumferential surface 2g of the main body portion 2 and the inner circumferential surface 5n of the sheath portion 5. In other words, the part of the outer circumferential surface 2g of the main body portion 2 facing the housing portion 8y may have a higher contact angle than the other parts on the outer circumferential surface 2g of the main body portion 2 and the inner circumferential surface 5n of the sheath portion 5.

More specifically, hydrophobic coating may be applied to the part of the outer circumferential surface 2g of the main body portion 2 facing the housing portion 8y. Hydrophilic coating may be applied to the other parts on the outer circumferential surface 2g of the main body portion 2 and the inner circumferential surface 5n of the sheath portion 5.

Note that examples of the hydrophobic coating include coating performed using a fluorine-based coating material. Examples of the hydrophilic coating include coating by bioinspire, PEG, and other hydrophilic polymers.

Naturally, it is also possible that coating is not performed and only the part of the outer circumferential surface 2g of the main body portion 2 facing the housing portion 8y is formed of fluorine-based resin such as PTFE, PE, or the like, whereby the part of the outer circumferential surface 2g of the main body portion 2 facing the housing portion 8y has higher hydrophobicity than the other parts on the outer circumferential surface 2g of the main body portion 2 and the inner circumferential surface 5n of the sheath portion 5.

When the part of the outer circumferential surface 2g of the main body portion 2 facing the housing portion 8y has higher hydrophobicity than the other parts on the outer circumferential surface 2g of the main body portion 2 and the inner circumferential surface 5n of the sheath portion 5 in this way, since the specimen contains fat as a main component, the specimen tends to adhere to a hydrophobic material. That is, the specimen tends to adhere to the part of the outer circumferential surface 2g of the main body portion 2 facing the housing portion 8y.

Therefore, if the specimen is attracted to the part of the outer circumferential surface 2g of the main body portion 2 facing the housing portion 8y, the specimen is housed in an attracted state to be opposed to the specimen collection port 150. Therefore, after surgery, the specimen can be easily extracted by tweezers or the like via the specimen collection port 150.

This is because, if the specimen adheres to the inner circumferential surface 5n of the sheath portion 5 in the housing portion 8y, since the inner circumferential surface 5n is located further on the specimen collection port 150 side than the outer circumferential surface 2g of the main body portion 2, after surgery, it is difficult to extract the specimen via the specimen collection port 150.

Further, as shown in FIG. 1 to FIG. 3, in the housing portion 8y, more specifically, on a distal end side in the axial direction E of the distal end face 5m and the inner circumferential surface 5n of the sheath portion 5, an edge portion 7 having a predetermined length E1 from the distal end 5s of the sheath portion 5 along the axial direction E and configured to cut a specimen housed in the housing portion 8y is provided.

The edge portion 7 cuts, for example, a ring-like specimen housed in the housing portion 8y and forms the specimen, for example, in a C shape to make it easy to extract, after surgery, the specimen from the housing portion 8y using tweezers or the like via the specimen collection port 150.

This is because, since the specimen collected by being nipped by the proximal end 3k and the distal end 5s is housed in a ring shape in the housing portion 8y, if the specimen keeps the ring shape, after surgery, it is difficult to extract the specimen via the specimen collection port 150. Alternatively, this is because, if the specimen keeps the ring shape, when the specimen is extracted, the specimen has to be cut by scissors or the like in a state in which the specimen is grasped by the tweezers and extraction work is complicated.

Note that, in the present embodiment, for example, one edge portion 7 is provided in the housing portion 8y. However, a plurality of the edge portions 7 may be provided along a circumferential direction of the housing portion 8y.

As shown in FIG. 4, in a halfway position in the axial direction E of the ultrasound probe system 1, more specifically, in a position further forward in the axial direction E than the below-mentioned connector 40 (see FIG. 14) in the main body portion 2, an operation member 21 of the main body portion 2 configured to move the main body portion 2 forward and backward in the axial direction E on an inside of the sheath portion 5 is fixed to the main body portion 2 by bonding, welding, or the like. Note that a position of the operation member 21 shown in FIG. 4 indicates a position where the specimen collection port 150 is in the closed state in which the proximal end 3k and the distal end 5s come into contact with each other shown in FIG. 1.

The operation member 21 is a member located outside the subject and operated by an examiner when the ultrasound probe system 1 is inserted into the subject. A finger hook 22 for operation, on which a finger of the examiner is hooked, is provided at a proximal end in the axial direction E of the operation member 21. Note that the finger hook 22 may be provided integrally with the operation member 21 or may be separate from the operation member 21 and fixed to the operation member 21.

Therefore, in a state in which the finger is hooked on the finger hook 22, when the examiner moves the operation member 21 forward in the axial direction E from the position shown in FIG. 4 to a position shown in FIG. 5, the proximal end 3k of the distal end portion 3 separates from the distal end 5s of the sheath portion 5 forward in the axial direction E. Consequently, as shown in FIG. 2, the specimen collection port 150 changes to the open state.

On the contrary, when the operation member 21 is moved backward in the axial direction E from the position shown in FIG. 5 to the position shown in FIG. 4, the proximal end 3k of the distal end portion 3 comes into contact with the distal end 5s of the sheath portion 5. Consequently, as shown in FIG. 1, the specimen collection port 150 changes to the closed state.

As shown in FIG. 4 and FIG. 5, an operation member 23 of the sheath portion 5 is fixed to an outer circumference at a proximal end of the sheath portion 5 by bonding, welding, or the like.

The operation member 23 is a member located outside the subject and operated by the examiner when the ultrasound probe system 1 is inserted into the subject and is a member configured to move the sheath portion 5 back and forth in the axial direction E.

At a proximal end in the axial direction E of the operation member 23, a finger hook 24 for operation, on which the finger of the examiner is hooked, is provided. Note that the finger hook 24 may be provided integrally with the operation member 23 or may be separate from the operation member 23 and fixed to the operation member 23 by bonding, welding, screw fastening, or the like.

Further, a through-hole 23h piercing through the operation member 23 in a radial direction is formed in a part further forward in the axial direction E than a part where the finger hook 24 is provided on a proximal end side in the axial direction E of the operation member 23 and further backward in the axial direction E than the proximal end of the sheath portion 5. In the through-hole 23h, a pipe sleeve 25 for supplying fluid to the space 8 or discharging the fluid from the space 8 via the through-hole 23h is provided. Note that the pipe sleeve 25 has, for example, a lure pipe sleeve shape.

For example, when the saline is supplied to the space 8 or when liquid or gas is supplied to the space 8 when the specimen is removed from the housing portion 8y, a fluid supplying device is attached to the pipe sleeve 25. Besides, when the space 8 is decompressed to allow the specimen to enter the housing portion 8y in the open state of the specimen collection port 150 or when the specimen housed in the housing portion 8y is sucked and extracted via the pipe sleeve 25, a suction device is attached to the pipe sleeve 25.

An O-shaped ring 27 is provided further backward in the axial direction E than the through-hole 23h between an inner circumferential surface on the proximal end side in the axial direction E of the operation member 23 and an outer circumferential surface of the operation member 21.

The O-shaped ring 27 is a member configured to prevent the fluid in the space 8 from being discharged from the proximal end side in the axial direction E of the operation member 23 and prevent liquid on an outside from suddenly entering the space 8.

On an inner circumferential surface at the proximal end in the axial direction E of the operation member 23, a stopper member 28 for the O-shaped ring 27 having a ring shape is fixed to the operation member 23 by screwing, bonding, press fitting, or the like.

Note that, as shown in FIG. 7, a convex portion 28t may be provided on an inner circumferential surface 28n of the stopper member 28. As shown in FIG. 6, two concave portions 21p and 21q that are separated along the axial direction E and in which the convex portion 28t can be fit may be provided in a position opposed to the convex portion 28t on an outer circumferential surface 21g of the operation member 21.

With such a configuration, when the convex portion 28t is fit in the concave portion 21p as shown in FIG. 6, as shown in FIG. 1, the operation member 21, that is, the main body portion 2 is fixed in the position where the specimen collection port 150 is in the closed state in which the proximal end 3k comes into contact with the distal end 5s. When the convex portion 28t is fit in the concave portion 21q, as shown in FIG. 2, the operation member 21, that is, the main body portion 2 is fixed in the position where the specimen collection port 150 is in the open state in which the proximal end 3k separates from the distal end 5s.

Figure 8:
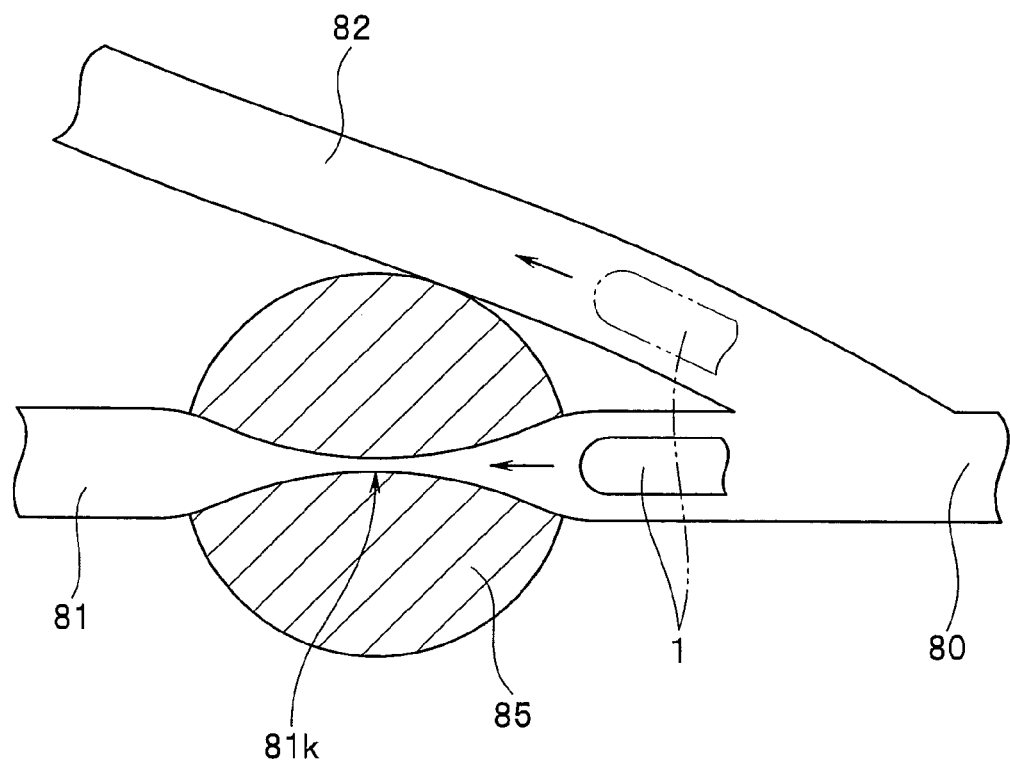
FIG. 8 is a diagram schematically showing a state in which the ultrasound probe system is inserted into one lumen having a narrow portion due to a lesion part and the other lumen without a lesion part in a branch portion of a pulmonary periphery in a subject.

Next, action in the present embodiment is explained with reference to FIG. 1 to FIG. 7 and FIG. 8. FIG. 8 is a diagram schematically showing a state in which the ultrasound probe system is inserted into one lumen having a narrow portion due to a lesion part and the other lumen without a lesion part in a branch portion of a pulmonary periphery in a subject.

First, outside the subject, the examiner inserts the main body portion 2 from the distal end side in the axial direction E of the sheath portion 5 into the inside of the sheath portion 5 along the axial direction E. Note that this work may be substituted by covering an outer circumference of the main body portion 2 with the sheath portion 5 from a proximal end side in the axial direction E of the main body portion 2 along the axial direction E.

Subsequently, the examiner injects the saline into the space 8. Note that as explained above, this injection work may be performed from the pipe sleeve 25 or may be performed from the specimen collection port 150 making use of the capillary phenomenon.

Thereafter, as shown in FIG. 6, the examiner fits the stopper member 28 in the concave portion 21p of the operation member 21 to thereby fix a position in the axial direction E of the main body portion 2 with respect to the sheath portion 5 in the closed state of the specimen collection port 150 shown in FIG. 1 in which the distal end 5s comes into contact with the proximal end 3k.

Subsequently, for example, when the examiner performs collection of a specimen of a small-diameter pulmonary periphery, into which the insertion portion 122a of the endoscope 122 cannot be inserted, using the ultrasound probe system 1, the examiner inserts the insertion portion 122a of the endoscope 122 into a bronchus via an oral cavity and, thereafter, after inserting the insertion portion 122a to a vicinity of an entrance of a pulmonary periphery bronchus, inserts, from the distal end side in the axial direction E, the ultrasound probe system 1 into the treatment instrument insert-through channel of the insertion portion 122a of the endoscope 122 from a treatment instrument insertion port 122e (see FIG. 20) of the treatment instrument insert-through channel provided in an operation portion 122b (see FIG. 20) of the endoscope 122.

Thereafter, after projecting a distal end side in the axial direction E of the ultrasound probe system 1 from a distal end opening of the insertion portion 122a of the treatment instrument insert-through channel, under X-ray observation, the examiner inserts the ultrasound probe system 1 into a target pulmonary periphery bronchus 80 as shown in FIG. 8 while checking a position of the distal end side in the axial direction E of the ultrasound probe system 1.

In this case, as explained above, since the stopper member 28 is fit in the concave portion 21p, that is, positions of the main body portion 2 and the sheath portion 5 are fixed, the closed state of the specimen collection port 150 is maintained. Therefore, since the proximal end 3k is in close contact with the distal end 5s, at least one of the proximal end 3k and the distal end 5s does not shave a wall surface of the pulmonary periphery bronchus 80, with which the ultrasound probe system 1 comes into contact, according to the insertion of the ultrasound probe system 1.

Since the positions of the main body portion 2 and the sheath portion 5 are fixed, the closed state of the specimen collection port 150 is maintained. Therefore, a situation is prevented in which, according to the insertion of the ultrasound probe system 1, the specimen collection port 150 is opened by the wall surface of the pulmonary periphery bronchus 80, with which the ultrasound probe system 1 comes into contact, and insertability of the ultrasound probe system 1 is deteriorated. Besides, as explained above, the wall surface of the pulmonary periphery bronchus 80 is prevented from being shaved by the distal end 5s and the proximal end 3k.

After inserting the ultrasound probe system 1 into the pulmonary periphery bronchus 80, the examiner searches for a lesion part 85 while performing ultrasound observation using the ultrasound observation portion 13.

In this case, when the examiner can recognize from an observation image of the ultrasound observation portion 13 that, as shown in FIG. 8, the distal end side in the axial direction E of the ultrasound probe system 1 is inserted into a lumen 82 without the lesion part 85 from a branch of the pulmonary periphery bronchus 80, more specifically, when the examiner recognizes from the observation image that the distal end side in the axial direction E of the ultrasound probe system 1 is not inserted into a center of the lesion part 85, the examiner pulls out the distal end side in the axial direction E of the ultrasound probe system 1 from the lumen 82 and inserts the distal end side in the axial direction E of the ultrasound probe system 1 into another lumen 81.

As a result, when the examiner can recognize from the observation image of the ultrasound observation portion 13 that, as shown in FIG. 8, the distal end side in the axial direction E of the ultrasound probe system 1 is located in the center of the lesion part 85 from the branch of the pulmonary periphery bronchus 80 and inserted into the lumen 81 in which a narrow portion 81k is formed by the lesion part 85, the examiner locates a distal end in the axial direction E of the ultrasound probe system 1 on an examiner's side about 1 cm from the center of the lesion part 85.

Thereafter, the examiner moves the main body portion 2 forward in the axial direction E by, about 1 cm from a position shown in FIG. 6 to a position shown in FIG. 5 using the operation member 21. As a result, the diameter of the narrow portion 81k is expanded by the distal end portion 3 and, as shown in FIG. 2, the proximal end 3k in contact with the distal end 5s moves forward in the axial direction E, whereby the specimen collection port 150 is opened.

According to the opening of the specimen collection port 150, since the narrow portion 81k is formed in the lumen 81 in which the lesion part 85 is formed, a part of the lesion part 85 is introduced into the sheath portion 5 to a vicinity of the outer circumferential surface 2g on a distal end side in the axial direction of the main body portion 2 via the specimen collection port 150. In this case, if the suction device is attached to the pipe sleeve 25 to decompress the space 8, the part of the lesion part 85 easily enters the sheath portion 5 more surely.

According to the opening of the specimen collection port 150, the ultrasound observation portion 13 moves forward about 1 cm in the axial direction E. However, in most cases, 2 cm or more of the lesion part 85 is present in the axial direction E, the ultrasound observation portion 13 does not lose sight of the lesion part 85 according to the movement.

Thereafter, after confirming from the observation image that a lesion part is rendered, the examiner adjusts a position in the axial direction E of the main body portion 2 or the sheath portion 5 according to necessity while observing the observation image in the ultrasound observation portion 13.

Subsequently, in order to collect a large volume of specimen of the lesion part 85, the examiner moves the main body portion 2 back and forth in the axial direction E or moves the sheath portion 5 back and forth in the axial direction E using the operation member 23.

As a result, a living tissue of the lesion part 85 is housed in the housing portion 8y via the specimen collection port 150 as a specimen by at least one of the distal end 5s and the proximal end 3k. Note that, in this case, when the suction device is attached to the pipe sleeve 25 to decompress the space 8, the specimen can be more easily housed in the housing portion 8y. Note that when the space 8 is decompressed, a collection quantity of specimen can be increased. Further, it is possible to collect specimen even in a bronchus with a slightly larger inner lumen.

A ring-like specimen housed in the housing portion 8y is partially cut in the edge portion 7 and formed in, for example, a C shape. If, for example, hydrophobic coating is applied to a part on the outer circumferential surface 2g of the main body portion 2 facing the housing portion 8y as explained above, the specimen is attracted to the part on the outer circumferential surface 2g of the main body portion 2 facing the housing portion 8y.

Thereafter, the examiner moves the main body portion 2 backward in the axial direction E until the stopper member 28 fits in the concave portion 21p and pulls out the ultrasound probe system 1 from the treatment instrument insert-through channel of the endoscope 122, that is, pulls out the ultrasound probe system 1 to an outside of the subject.

Subsequently, on the outside of the subject, the examiner moves the main body portion 2 forward in the axial direction E again or moves the sheath portion 5 backward in the axial direction E to thereby change the specimen collection port 150 to the open state as shown in FIG. 2. Thereafter, the examiner extracts, using the tweezers or the like, via the specimen collection port 150, the specimen housed in the housing portion 8y on the outer circumferential surface 2g of the main body portion 2 and cut by the edge portion 7.

Note that the extraction of the specimen may be performed by immersing the distal end side in the axial direction E of the ultrasound probe system 1 in liquid to thereby drop the specimen into the liquid. Further, the extraction of the specimen may be performed by supplying the liquid from the pipe sleeve 25 to the space 8 or may be performed by sucking the liquid from the pipe sleeve 25 via the space 8.

Thereafter, after the extraction of the specimen ends, the examiner moves the main body portion 2 backward in the axial direction E until the stopper member 28 fits in the concave portion 21p or moves the sheath portion 5 forward in the axial direction E to bring the proximal end 3k into contact with the distal end 5s. That is, the examiner changes the specimen collection port 150 to the closed state as shown in FIG. 1.

Finally, the examiner discards the sheath portion 5 and the main body portion 2.

As explained above, in the present embodiment, during the ultrasound observation of the lesion part 85 by the ultrasound observation portion 13, the main body portion 2 is moved back and forth in the axial direction E or the sheath portion 5 is moved back and forth in the axial direction E. Consequently, it is possible to collect the specimen of the lesion part 85 using at least one of the proximal end 3k of the distal end portion 3 and the distal end 5s of the sheath portion 5.

Therefore, during the ultrasound observation of the lesion part 85 by the ultrasound observation portion 13, it is possible to collect the specimen of the lesion part 85 surely and with high position accuracy.

In the present embodiment, the edge portion 7 configured to cut the specimen housed in the housing portion 8y is provided in the housing portion 8y.

Further, the part of the outer circumferential surface 2g of the main body portion 2 facing the housing portion 8y has more hydrophobicity than the other parts on the outer circumferential surface 2g of the main body portion 2 and the inner circumferential surface 5n of the sheath portion 5.

Therefore, the specimen housed in the housing portion 8y is cut by the edge portion 7. The specimen adheres to the part of the outer circumferential surface 2g of the main body portion 2 facing the housing portion 8y. Consequently, it is possible to easily collect the specimen from the housing portion 8y via the specimen collection port 150.

Therefore, certainty of diagnostic properties for a lesion part is improved. A reduction in an examination time and reexamination are unnecessary. Therefore, it is possible not only to reduce burdens on the examiner and the subject but also, for example, to select an appropriate method of treatment.

Consequently, it is possible to provide the ultrasound probe system 1 including a configuration with which collection of a specimen of an examined region can be performed during ultrasound observation and the collected specimen is easily extracted.

Figure 9:
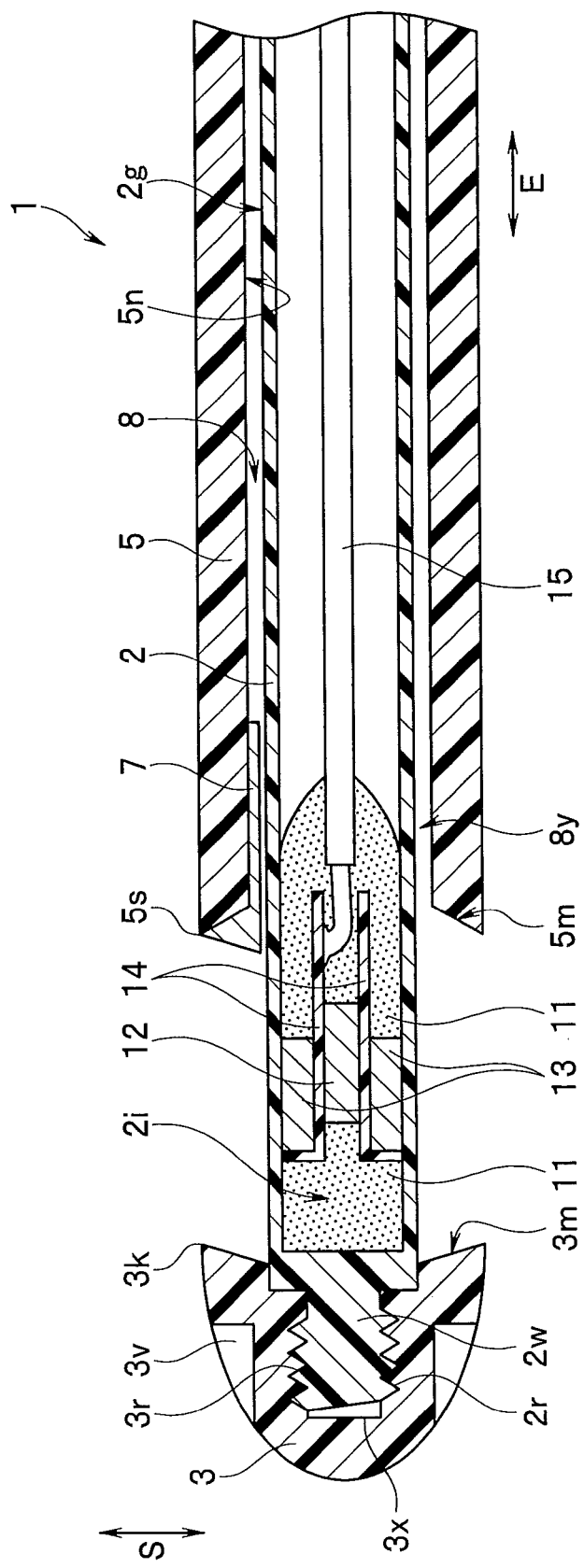
FIG. 9 is a partial sectional view of the distal end side in the axial direction of the ultrasound probe system showing a configuration in which the distal end portion is detachable from the main body portion shown in FIG. 1.

Note that a modification is explained below with reference to FIG. 9. FIG. 9 is a partial sectional view of the distal end side in the axial direction of the ultrasound probe system showing a configuration in which the distal end portion is detachable from the main body portion shown in FIG. 1.

In the present embodiment explained above, the distal end portion 3 is formed integrally with the main body portion 2. However, the distal end portion 3 is not limited to this and may be provided separately from the main body portion 2.

More specifically, as shown in FIG. 9, a small-diameter portion 2w, on an outer circumferential surface of which a screw 2r is formed, is formed at the distal end in the axial direction E of the main body portion 2. At the distal end portion 3, a concave groove 3x along the axial direction E, in which the small-diameter portion 2w can be fit, is formed in a center in a radial direction of the distal end portion 3. Further, a screw groove 3r, with which the screw 2r is screwed, is formed on an inner circumferential surface of the concave groove 3x. On the outer circumferential surface of the distal end portion 3, a rotation groove 3v for rotating the distal end portion 3 in order to fix the distal end portion 3 to the small-diameter portion 2w is formed.

Therefore, the distal end portion 3 can be attached to a distal end in the axial direction E of the main body portion 2 simply by fitting the small-diameter portion 2w in the concave groove 3x, rotating the distal end portion 3 in one direction using the rotation groove 3v, and screwing the screw 2r in the screw groove 3r. The distal end portion 3 can be pulled out from the distal end in the axial direction E of the main body portion 2 simply by rotating the distal end portion 3 in the other direction using the rotation groove 3v and removing the small-diameter portion 2w from the concave groove 3x.

With such a configuration, since the distal end portion 3 including the proximal end 3k configured to collect a specimen can be removed from the main body portion 2. Therefore, if the distal end portion 3 is removed, an outer surface of the main body portion 2 can be cleaned, disinfected, and sterilized. Therefore, the main body portion 2 can be used again. According to a purpose, it is possible to mount, on the main body portion 2, a plurality of kinds of the distal end portion 3 having different angles of the proximal end 3k.

Note that the other effects are the same as the effects in the first embodiment.

(Second Embodiment)

Figure 10:
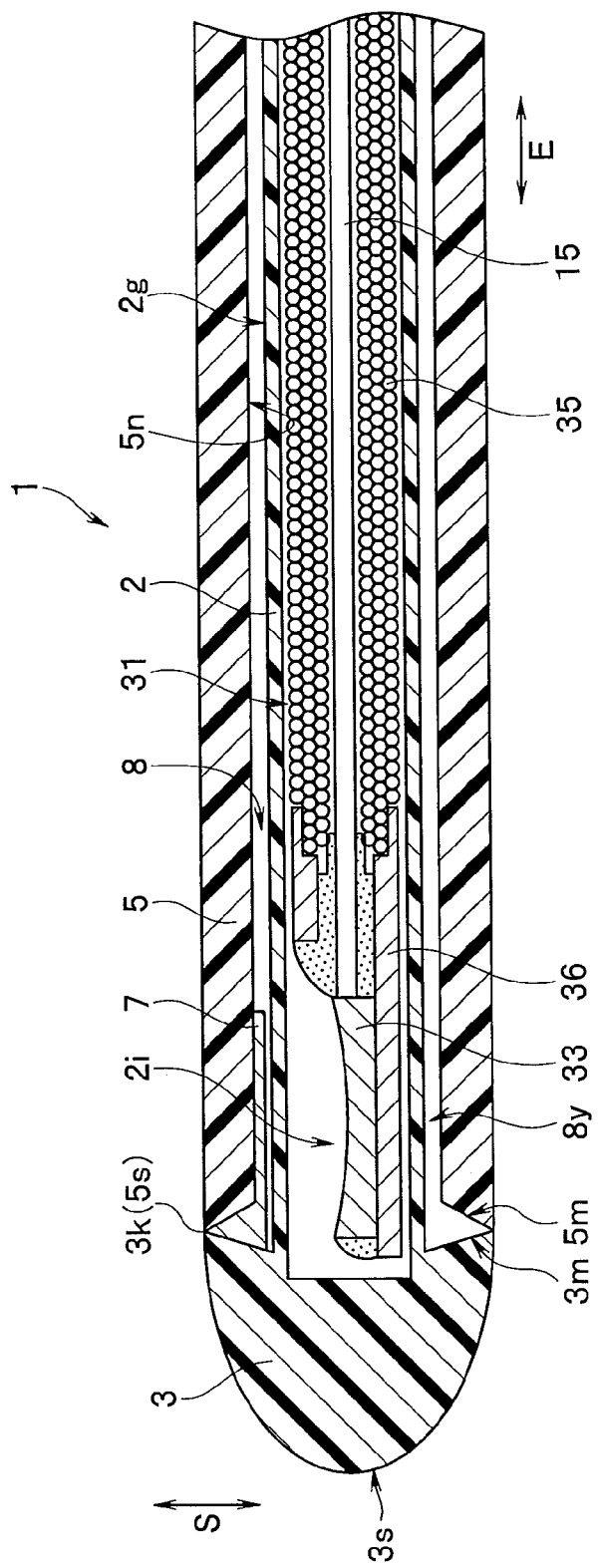
FIG. 10 is a partial sectional view showing, in a closed state of a specimen collection port, a distal end side in an axial direction of an ultrasound probe system in a second embodiment.
Figure 11:
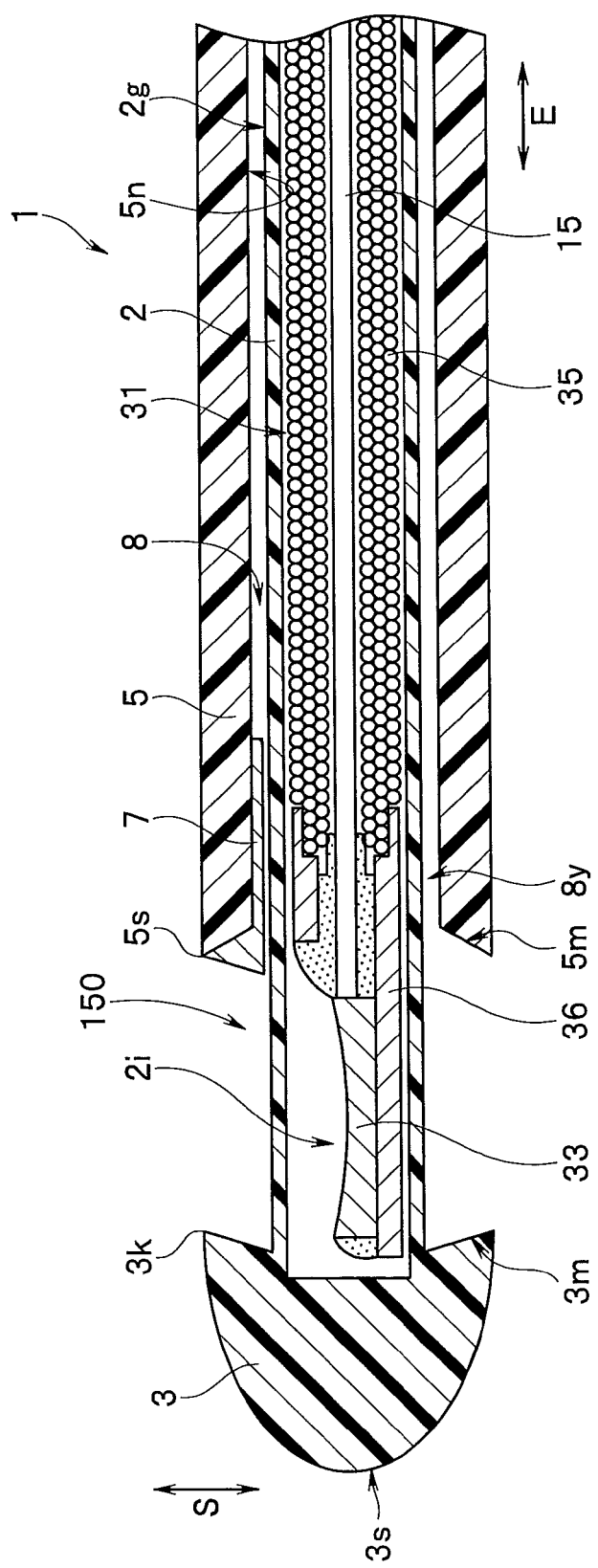
FIG. 11 is a partial sectional view showing the distal end side in the axial direction of the ultrasound probe system in an open state of the specimen collection port shown in FIG. 10.

FIG. 10 is a partial sectional view showing, in a closed state of a specimen collection port, a distal end side in an axial direction of an ultrasound probe system in the present embodiment. FIG. 11 is a partial sectional view showing the distal end side in the axial direction of the ultrasound probe system in an open state of the specimen collection port shown in FIG. 10.

Figure 12:
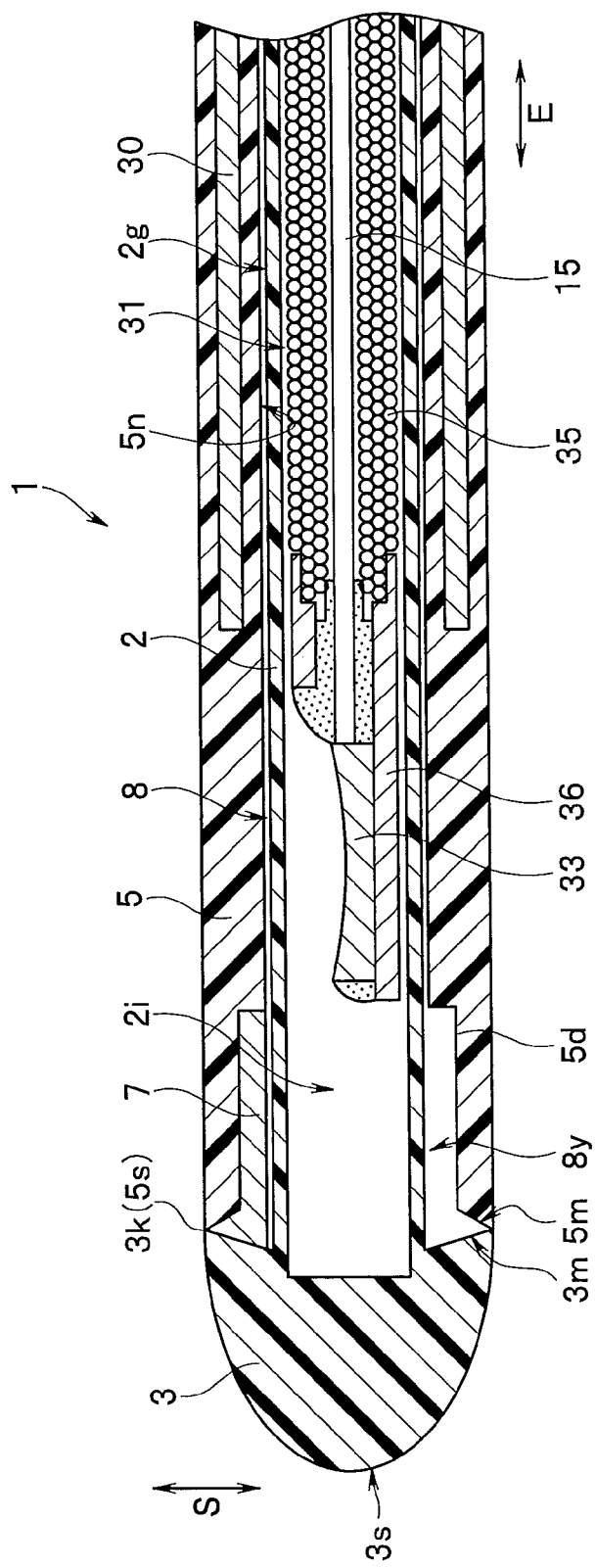
FIG. 12 is a partial sectional view of the distal end side in the axial direction of the ultrasound probe system showing, in the closed state of the specimen collection port, a modification in which a step portion is provided in a part on an inner circumferential surface of a sheath portion facing a housing portion shown in FIG. 10.
Figure 13:
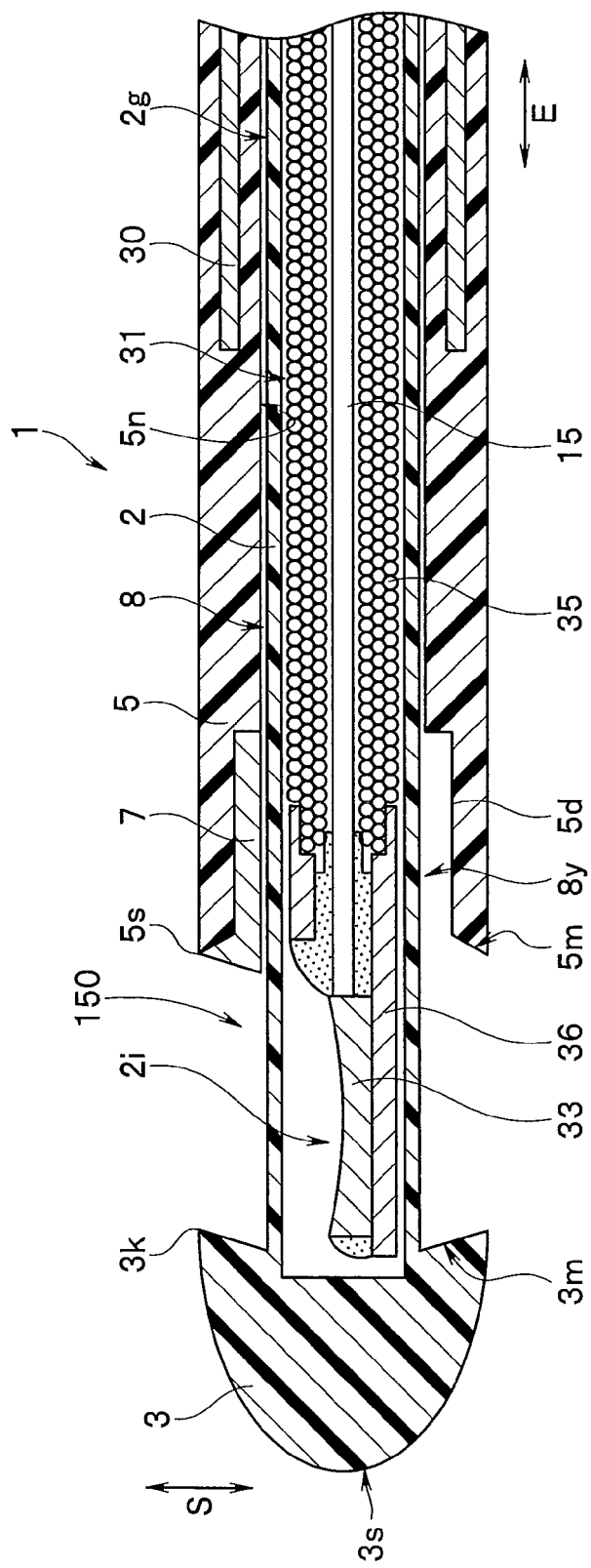
FIG. 13 is a partial sectional view showing the distal end side in the axial direction of the ultrasound probe system in the open state of the specimen collection port shown in FIG. 12.
Figure 14:
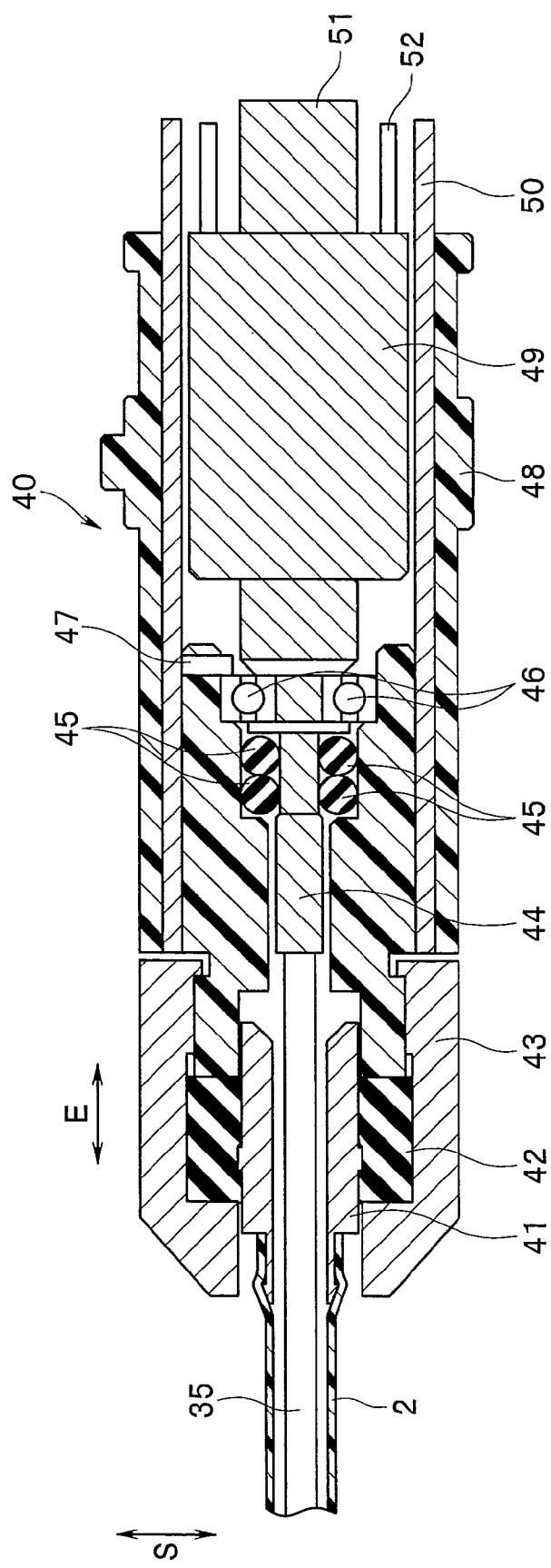
FIG. 14 is a partial sectional view schematically showing a connector provided at a proximal end of the ultrasound probe system shown in FIG. 10.

FIG. 12 is a partial sectional view of the distal end side in the axial direction of the ultrasound probe system showing, in the closed state of the specimen collection port, a modification in which a step portion is provided in a part on an inner circumferential surface of a sheath portion facing a housing portion shown in FIG. 10. FIG. 13 is a partial sectional view showing the distal end side in the axial direction of the ultrasound probe system in the open state of the specimen collection port shown in FIG. 12. FIG. 14 is a partial sectional view schematically showing a connector provided at a proximal end of the ultrasound probe system shown in FIG. 10.

Compared with the ultrasound probe system in the first embodiment shown in FIG. 1 to FIG. 8, a configuration of the ultrasound probe system in the second embodiment is different in that an ultrasound observation portion 33 is provided movably back and forth in the axial direction in the main body portion 2.

Therefore, only the difference is explained. Components same as the components in the first embodiment are denoted by the same reference numerals and signs and explanation of the components is omitted.

As shown in FIG. 10 and FIG. 11, in the present embodiment, on the inside 2i of the main body portion 2, the ultrasound observation portion 33 that transmits ultrasound in the side surface direction S of the main body portion 2 to thereby obtain an ultrasound image in a subject is provided to be movable back and forth in the axial direction E.

More specifically, the ultrasound observation portion 33 is provided at a distal end in the axial direction E of an ultrasound probe 31 housed to be movable back and forth in the axial direction E on the inside 2i of the main body portion 2. That is, the ultrasound probe 31 including the ultrasound observation portion 33 is provided to be not fixed to the main body portion 2.

More specifically, the ultrasound probe 31 is configured from a mechanical radial scanning probe.

The ultrasound probe 31 includes the ultrasound observation portion 33 located at the distal end in the axial direction E and configured from a single ultrasound transducer, a housing 36 configured to retain the ultrasound observation portion 33, and the ultrasound transducer cable 15 extended backward in the axial direction E from the ultrasound observation portion 33 to the below-mentioned connector 40 (see FIG. 14) and configured to transmit, to the ultrasound observation portion 33, an electric pulse signal outputted from the below-mentioned ultrasound observation device 123 (see FIG. 20).

The ultrasound probe 31 includes a flexible shaft 35 including the ultrasound transducer cable 15 and extended backward in the axial direction E from the housing 36. The flexible shaft 35 gives rotation power to the housing 36. That is, the ultrasound observation portion 33 rotates together with the housing 36 with the rotation power given by the flexible shaft 35.

As shown in FIG. 14, in the connector 40 provided at the proximal end in the axial direction E of the ultrasound probe system 1, for example, in a connector cover 48 formed of resin, a proximal end in the axial direction E of the flexible shaft 35 is connected to a connector main body 49 via a rotation transmission shaft 44 and a bearing 46 prevented from coming off the connector cover 48 by a fixing pin 47. When an electric connector 51 and rotation transmission pins 52 extending from the connector main body 49 are connected to the ultrasound observation device 123, a rotation driving force is transmitted to the flexible shaft 35 from a driving source provided in the ultrasound observation device 123. Note that the connector main body 49 is fixed to the connector cover 48 by the fixing pin 47.

In the connector 40, a shield cover 50 for noise reduction formed of metal such as stainless steel or a copper alloy is provided between the connector cover 48 and the connector main body 49.

The rotation transmission shaft 44 is in contact with an inner circumferential surface of the connector cover 48 via an O-shaped ring 45. A sheath fixing ring 43 is pivotably screwed with a screw formed on an outer circumference on a distal end side in the axial direction E of the connector cover 48.

On an inside of the sheath fixing ring 43, a sheath fixing pipe sleeve 41, to which the proximal end in the axial direction E of the main body portion 2 is fixed, is provided. A rubber ring 42 is provided between an outer circumference of the sheath fixing pipe sleeve 41 and an inner circumference of the sheath fixing ring 43.

The sheath fixing ring 43 compresses the rubber ring 42 in a radial direction according to rotation. When the rubber ring 42 is compressed in the radial direction, an inner diameter of the rubber ring 42 decreases and the rubber ring 42 comes into contact with an outer circumferential surface of the sheath fixing pipe sleeve 41. Consequently, a position at the proximal end in the axial direction E of the main body portion 2 is fixed.

Note that, although not shown in the figure, in the present embodiment, as in the first embodiment, as shown in FIG. 4 and FIG. 5, the operation member 21 configured to move the main body portion 2 back and forth in the axial direction E, and the operation member 23 configured to move the sheath portion 5 back and forth in the axial direction E, is provided further forward in the axial direction E than the connector 40 in a halfway position in the axial direction E of the ultrasound probe system 1.

In the present embodiment, as in the first embodiment, as shown in FIG. 6, the ultrasound probe system 1 may include a structure for fixing a position in the axial direction E of the main body portion 2 with respect to the sheath portion 5 using fitting of the stopper member 28 provided in the operation member 23 in the concave portions 21p and 21q provided in the operation member 21.

In the present embodiment, an ultrasound transmission medium is filled on the inside 2i of the main body portion 2. Note that examples of the ultrasound transmission medium filled in the inside 2i include sterilized water, distilled water, and liquid paraffin.

As shown in FIG. 12 and FIG. 13, in the sheath portion 5, a part facing the housing portion 8y is formed thinner in the radial direction than other parts. Therefore, a step portion 5d having a predetermined length from the distal end of the sheath portion 5 may be formed on the inner circumferential surface 5n.

If the step portion 5d is formed in a part of the inner circumferential surface 5n facing the housing portion 8y, even if the space 8 between the outer circumferential surface 2g of the main body portion 2 and the inner circumferential surface 5n of the sheath portion 5 is extremely narrow as shown in FIG. 12 and FIG. 13, it is possible to secure a large housing space for a specimen using the step portion 5d.

The surface treatment for increasing hydrophobicity may be applied to a part of the outer circumferential surface 2g of the main body portion 2 opposed to the inner circumferential surface 5n formed by the step portion 5d of the sheath portion 5. In other words, the part of the outer circumferential surface 2g of the main body portion 2 facing the housing portion 8y may have a higher contact angle than the other parts on the outer circumferential surface 2g of the main body portion 2 not facing the housing portion 8y and the inner circumferential surface 5n formed by the step portion 5d.

More specifically, the hydrophobic coating may be applied to the part of the outer circumferential surface 2g of the main body portion 2 facing the housing portion 8y. The hydrophilic coating may be applied to the other parts on the outer circumferential surface 2g of the main body portion 2 not facing the housing portion 8y and the inner circumferential surface 5n formed by the step portion 5d of the sheath portion 5.

Naturally, it is also possible that coating is not performed and only the part of the outer circumferential surface 2g of the main body portion 2 facing the housing portion 8y is formed of fluorine-based resin such as PTFE, PE, or the like, whereby the part of the outer circumferential surface 2g of the main body portion 2 facing the housing portion 8y has higher hydrophobicity than the other parts on the outer circumferential surface 2g of the main body portion 2 and the inner circumferential surface 5n formed by the step portion 5d of the sheath portion 5.

When the part of the outer circumferential surface 2g of the main body portion 2 facing the housing portion 8y has higher hydrophobicity than the other parts on the outer circumferential surface 2g of the main body portion 2 and the inner circumferential surface 5n formed by the step portion 5d of the sheath portion 5 in this way, since the specimen contains fat as a main component, the specimen tends to adhere to a hydrophobic material. That is, the specimen tends to adhere to the part of the outer circumferential surface 2g of the main body portion 2 facing the housing portion 8y.

Note that the step portion 5d may be formed on the inner circumferential surface 5n of the sheath portion 5 of the ultrasound probe system 1 in the first embodiment.

Note that a part opposed to the ultrasound observation portion 33 on the distal end side in the axial direction E of the sheath portion 5 has ultrasound permeability.

Further, in the sheath portion 5, a blade 30 may be provided along the axial direction E in a part through which ultrasound transmitted from the ultrasound observation portion 33 to the side surface direction S does not pass. Therefore, since stretchability in the axial direction E of the sheath portion 5 is deteriorated by the blade 30, as shown in FIG. 10 and FIG. 12, the specimen collection port 150 is prevented from suddenly opening when the specimen collection port 150 is inserted into the lesion part 85 in the pulmonary periphery bronchus 80 on the distal end side in the axial direction E of the ultrasound probe system 1 in the closed state.

Note that the other components are the same as the components in the first embodiment.

Next, action in the present embodiment is explained.

First, an examiner takes out the sheath portion 5 and the main body portion 2 from a sterilized pack and fills the ultrasound transmission medium in the inside 2i of the main body portion 2.

Subsequently, the examiner inserts the ultrasound probe system 1 into the inside 2i of the main body portion 2 and rotates the sheath fixing ring 43 (see FIG. 14) to thereby fix the proximal end in the axial direction E of the main body portion 2 as explained above.

Thereafter, a step of filling saline in the space 8, a step of inserting the distal end side in the axial direction E of the ultrasound probe system 1 to the pulmonary periphery bronchus 80, a step of collecting a specimen of the lesion part 85 using the proximal end 3k and the distal end 5s to be housed in the housing portion 8y, and a step of extracting the specimen housed in the housing portion 8y outside the subject after the collection are the same as the steps in the first embodiment explained above. Therefore, explanation of the steps is omitted.

Note that, in the present embodiment, when the ultrasound probe system 1 is inserted in the pulmonary periphery bronchus 80 as shown in FIG. 8, as shown in FIG. 14, the proximal end in the axial direction E of the main body portion 2 is fixed using the sheath fixing pipe sleeve 41, the rubber ring 42, and the sheath fixing ring 43. In addition, the main body portion 2 has higher stretchability in the axial direction E than the sheath portion 5. Therefore, the stopper member 28 fits in the concave portion 21p as shown in FIG. 6. In a state in which the proximal end 3k of the distal end portion 3 is in contact with the distal end 5s of the sheath portion 5 with pressure backward in the axial direction E (the closed state of the specimen collection port shown in FIG. 6 corresponding to FIG. 4), as shown in FIG. 12, the distal end portion 3 is pressed forward in the axial direction E by the distal end 5s of the sheath portion 5, whereby the main body portion 2 expands forward in the axial direction E. As a result, the ultrasound probe 31 is in a state in which the ultrasound probe 31 moves backward in the axial direction E on the inside 2i of the main body portion 2.

Finally, after extracting the specimen from the housing portion 8y, the examiner discards the main body portion 2 and the sheath portion 5. Thereafter, after cleaning the ultrasound probe 31 taken out from the inside 2i of the main body portion 2, the examiner puts the ultrasound probe 31 in a sterilized pack and sterilizes and stores the ultrasound probe 31.

As explained above, in the present embodiment, the ultrasound probe 31 including the ultrasound observation portion 33 is provided to be movable back and forth in the axial direction E on the inside 2i of the main body portion 2. That is, the ultrasound probe 31 including the ultrasound observation portion 33 is provided not to be fixed to the main body portion 2.

Therefore, after collection of the specimen, the main body portion 2 to which the distal end portion 3 provided with the proximal end 3k used for the specimen collection is fixed and the sheath portion 5 including the distal end 5s used for the specimen collection are discarded. However, the ultrasound probe 31 provided with the ultrasound observation portion 33 can be reused. Therefore, it is possible to perform specimen collection work at lower costs than in the first embodiment.

Note that the other effects are the same as the effects in the first embodiment.

Figure 15:
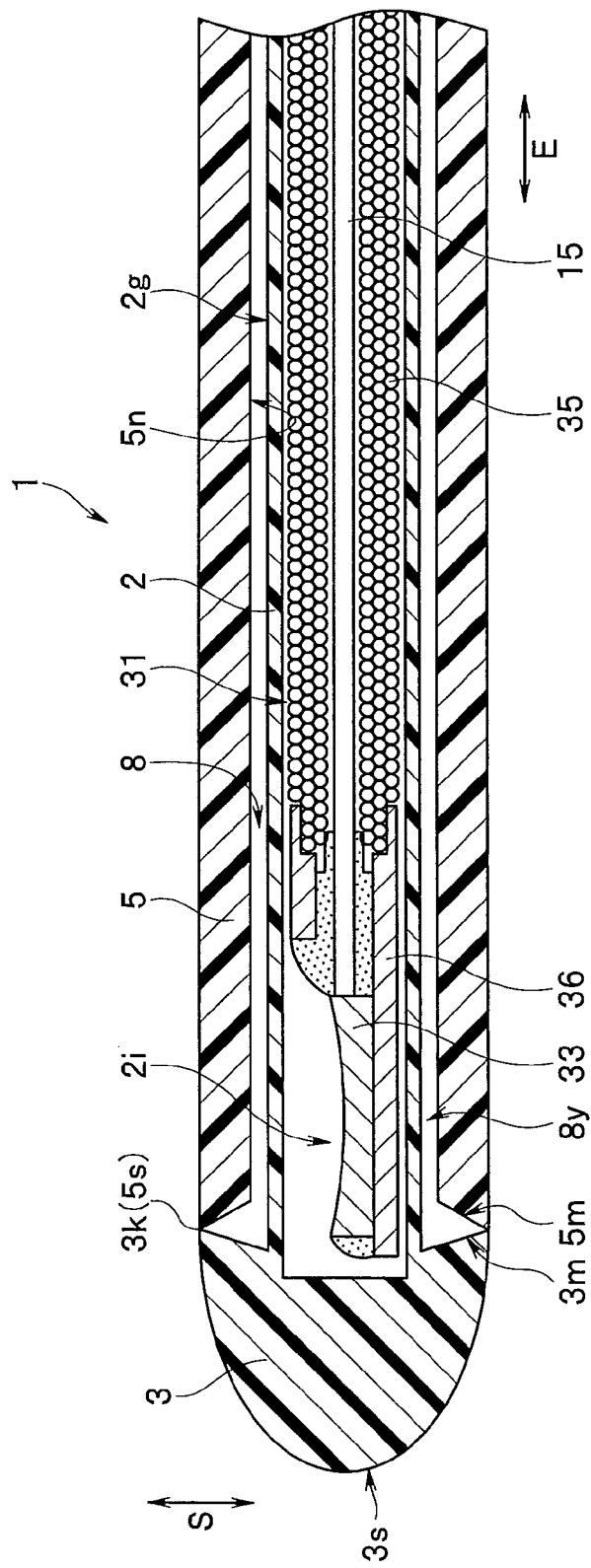
FIG. 15 is a partial sectional view of the distal end side in the axial direction of the ultrasound probe system showing a configuration of a modification excluding an edge portion from a housing portion of the ultrasound probe system shown in FIG. 10.

A modification of the present embodiment is explained with reference to FIG. 15. FIG. 15 is a partial sectional view of a distal end side in an axial direction of an ultrasound probe system showing a configuration of the modification in which the edge portion 7 is excluded from the housing portion 8y of the ultrasound probe system 1 shown in FIG. 10.

As shown in FIG. 15, the edge portion 7 does not have to be provided in the housing portion 8y. Therefore, it is difficult to extract the specimen housed in the housing portion 8y. Otherwise, effects same as the effects in the second embodiment can be obtained.

Figure 16:
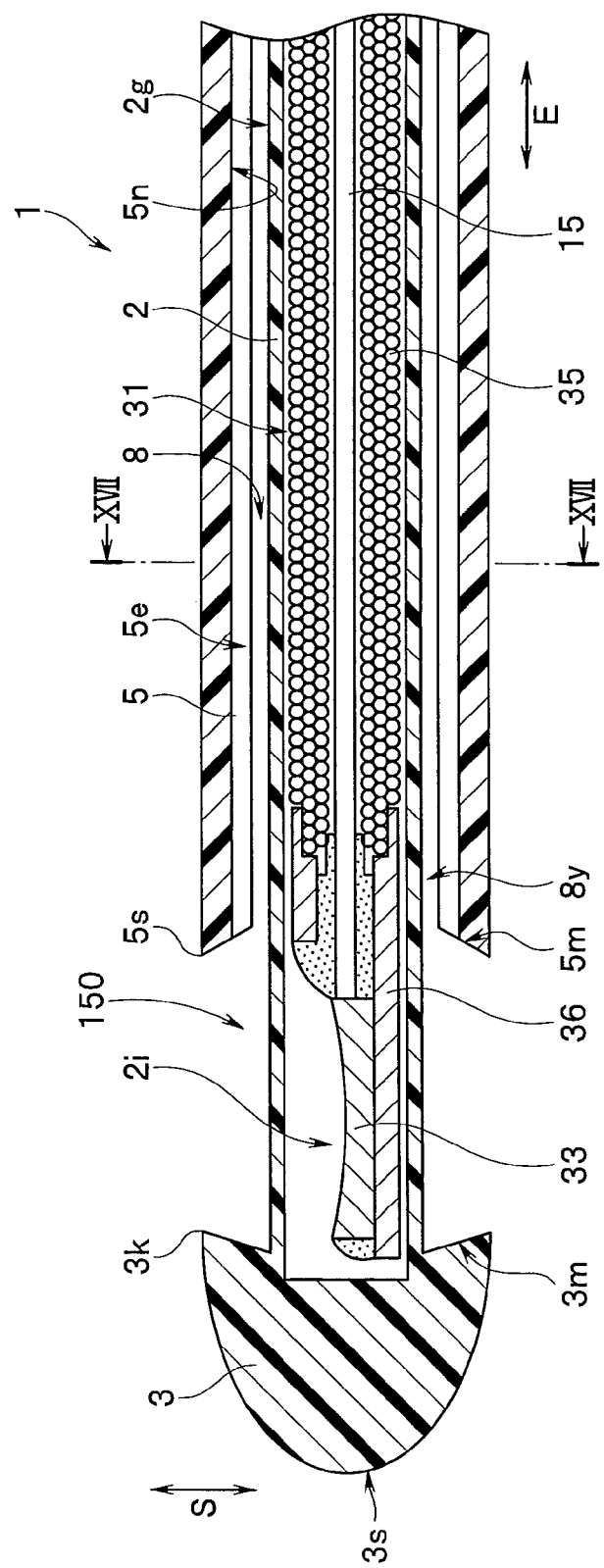
FIG. 16 is a partial sectional view of the distal end side in the axial direction of the ultrasound probe system showing a configuration of a modification in which a plurality of grooves along the axial direction are formed along a circumferential direction on an inner circumferential surface of the sheath portion of the ultrasound probe system shown in FIG. 10.
Figure 17:
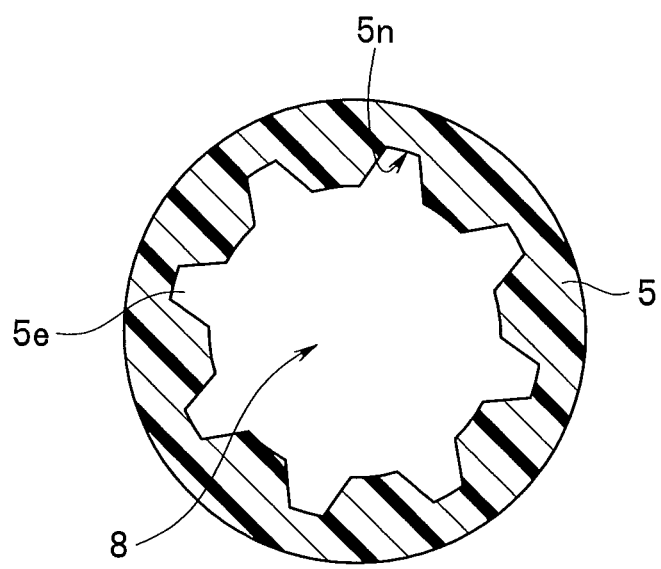
FIG. 17 is a sectional view of the sheath portion taken along line XVII-XVII in FIG. 16.

Another modification is explained below with reference to FIG. 16 and FIG. 17. FIG. 16 is a partial sectional view of the distal end side in the axial direction of the ultrasound probe system showing a configuration of a modification in which a plurality of grooves 5e along the axial direction are formed along a circumferential direction on the inner circumferential surface 5n of the sheath portion 5 of the ultrasound probe system 1 shown in FIG. 10. FIG. 17 is a sectional view of the sheath portion taken along line XVII-XVII in FIG. 16.

As shown in FIGS. 16 and 17, a plurality of grooves 5e along the axial direction E may be formed along the circumferential direction on the inner circumferential surface 5n of the sheath portion 5.

With such a configuration, the sheath portion 5 or the main body portion 2 can be smoothly moved back and forth in the axial direction E by the plurality of grooves 5e. A space of the housing portion 8y can be secured larger by a size of the groove 5e than in the present embodiment shown in FIG. 10. Besides, eccentricity of the sheath portion 5 with respect to the main body portion 2 can be suppressed as much as possible by the plurality of grooves 5e. Therefore, it is possible to surely collect a specimen. Note that the other effects are the same as the effects in the second embodiment.

Figure 18:
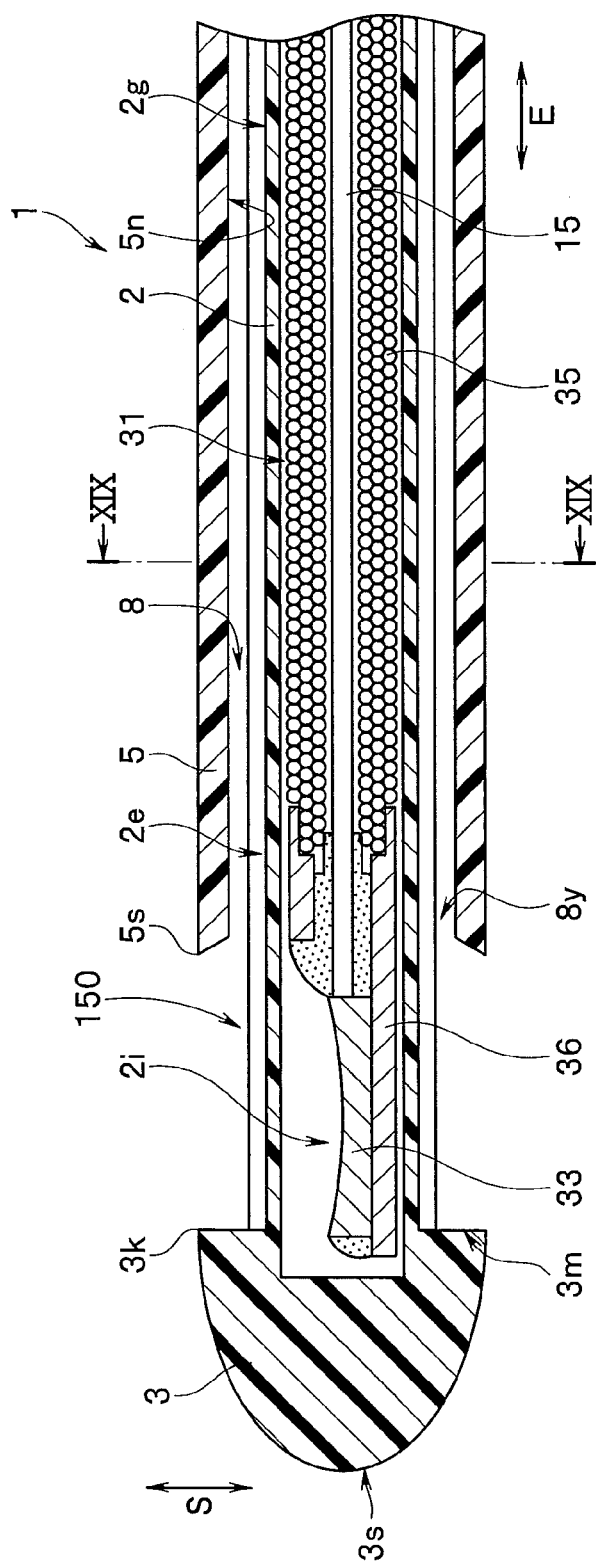
FIG. 18 is a partial sectional view of the distal end side in the axial direction of the ultrasound probe system showing a configuration of a modification in which a plurality of grooves along the axial direction are formed along the circumferential direction on an outer circumferential surface of the main body portion of the ultrasound probe system shown in FIG. 10.
Figure 19:
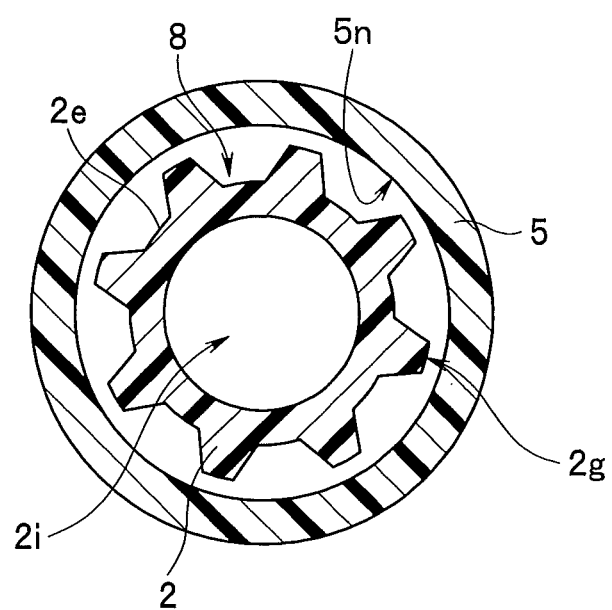
FIG. 19 is a sectional view of the sheath portion and the main body portion taken along line XIX-XIX in FIG. 18.

Another modification is explained below with reference to FIG. 18 and FIG. 19. FIG. 18 is a partial sectional view of the distal end side in the axial direction of the ultrasound probe system showing a configuration of a modification in which a plurality of grooves 2e along the axial direction are formed along the circumferential direction on the outer circumferential surface 2g of the main body portion 2 of the ultrasound probe system shown in FIG. 10. FIG. 19 is a sectional view of the sheath portion and the main body portion taken along line XIX-XIX in FIG. 18.

As shown in FIG. 18 and FIG. 19, the plurality of groves 2e along the axial direction E may be formed along the circumferential direction on the outer circumferential surface 2g of the main body portion 2.

With such a configuration, the sheath portion 5 or the main body portion 2 can be smoothly moved back and forth in the axial direction E by the plurality of grooves 2e. The space of the housing portion 8y can be secured larger by a size of the groove 2e than in the present embodiment shown in FIG. 10. Besides, eccentricity of the sheath portion 5 with respect to the main body portion 2 can be suppressed as much as possible by the plurality of grooves 2e. Therefore, it is possible to surely collect a specimen.

As shown in FIG. 18, the proximal end face 3m of the distal end portion 3 may be formed on a flat surface. That is, the proximal end 3k does not have to be formed at an acute angle. In this case, the proximal end 3k does not configure the specimen collecting portion.

That is, in such a configuration, only the distal end 5s of the sheath portion 5 configures the specimen collecting portion. With such a configuration, effects same as the effects in the second embodiment can be obtained.

The other effects are the same as the effects in the second embodiment.

Naturally, the configurations shown in FIG. 15 to FIG. 19 can also be applied to the ultrasound probe system in the first embodiment.

In the present embodiment, as shown in FIG. 9 in the first embodiment, the distal end portion 3 may be provided separately from the main body portion 2.

Figure 20:
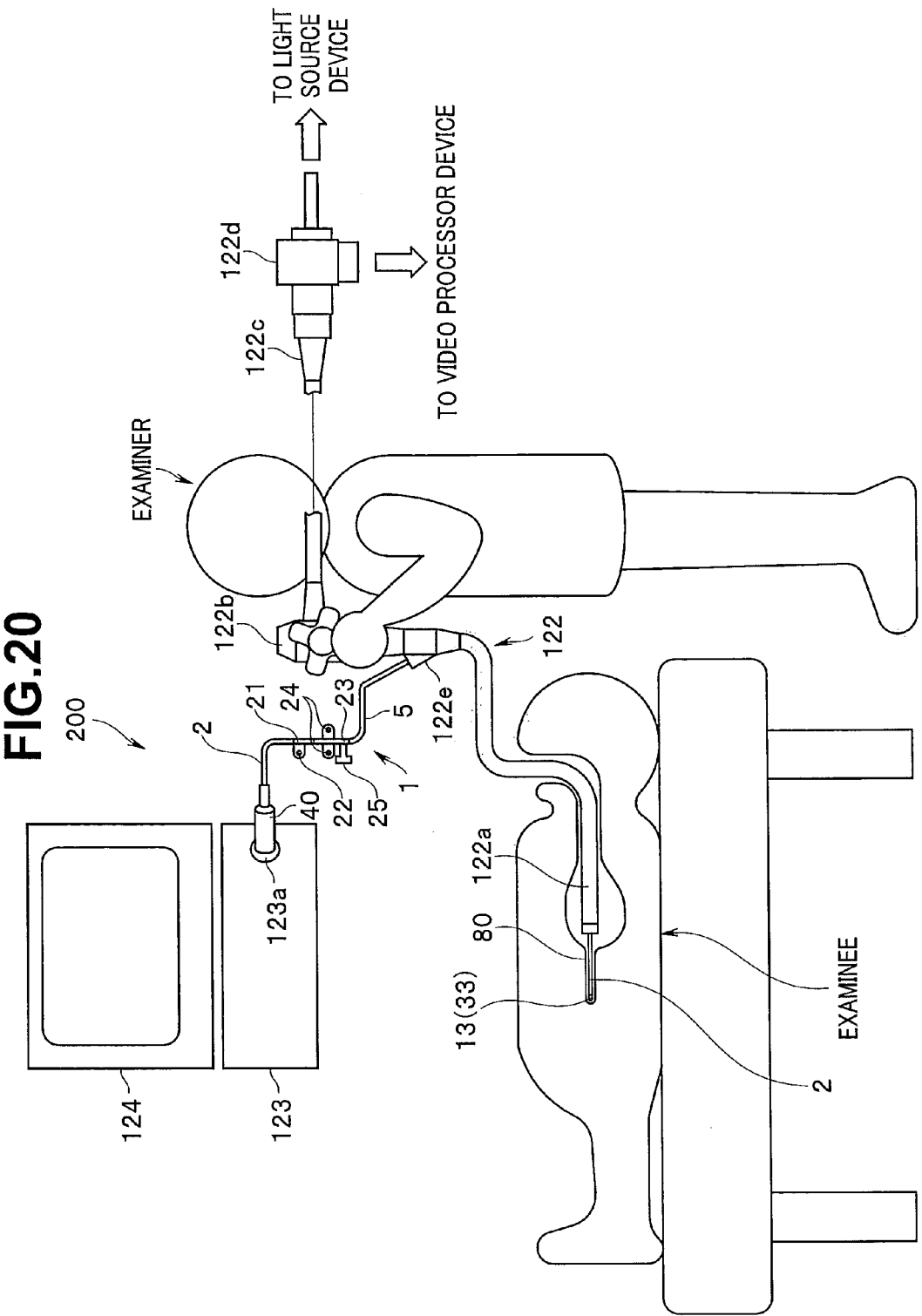
FIG. 20 is a diagram schematically showing an endoscope system including the ultrasound probe system in the first and second embodiments.

Note that the ultrasound probe system 1 in the first and second embodiments explained above is used in, for example, an endoscope system shown in FIG. 20.

FIG. 20 is a diagram schematically showing an endoscope system including the ultrasound probe system in the first and second embodiments.

As shown in FIG. 20, the endoscope 122 included in an endoscope system 200 includes the long endoscope insertion portion 122a having flexibility. The operation portion 122b is provided on an examiner's side of the endoscope insertion portion 122a.

Further, a universal cord 122c is extended from the operation portion 122b. A scope connector 122d is provided at an end portion of the universal cord 122c. A video processor device and a light source device not shown in the figure are connected to the scope connector 122d.

The treatment instrument insertion port 122e is opened near a coupling portion of the endoscope insertion portion 122a and the operation portion 122b. The treatment instrument insert-through channel communicates with the treatment instrument insertion port 122e. The treatment instrument insert-through treatment instrument channel is formed in the endoscope insertion portion 122a, and a distal end thereof is opened on a distal end face of the endoscope insertion portion 122a.

The connector 40 provided at the proximal end of the ultrasound probe system 1 is connected to a connector receiving portion 123a of the ultrasound observation device 123. The ultrasound observation device 123 causes a monitor 124 to display an ultrasound image obtained by the ultrasound observation portion 13 (33).

The present invention is not limited to the embodiments explained above and various alterations, modifications, and the like are possible in a range in which the gist of the present invention is not changed.

What is claimed is:

1. An ultrasound probe system comprising:
    a bar-like main body portion;
    an ultrasound observation portion provided in the main body portion and configured to transmit ultrasound in a side surface direction of the main body portion and receive a reflected wave;
    a distal end portion provided such that a proximal end face, which is a surface on a proximal end side, is adjacent to a distal end in an axial direction of the main body portion, the distal end portion having a diameter larger than the main body portion;
    a cylindrical sheath portion having a diameter larger than the main body portion and configured to house the main body portion on an inside thereof to be configured for advancing and retracting in the axial direction;
    a distal end face arranged at a distal end of the sheath portion and facing the proximal end face;
    a specimen collecting portion provided on at least one of the proximal end face and the distal end face, an entire circumference of the specimen collecting portion being formed at an acute angle toward the axial direction in order to separate a specimen from a subject in an annular shape; and
    an edge portion arranged on the proximal end face or the distal end face to cross the entire circumference of the specimen collecting portion in order to cut the annular specimen collected by the specimen collecting portion.

2. The ultrasound probe system according to claim 1, wherein the edge portion is formed on the distal end face.

3. The ultrasound probe system according to claim 1, wherein the main body portion has higher stretchability in the axial direction than the sheath portion.

4. The ultrasound probe system according to claim 1, wherein an outer circumferential surface of the main body portion has higher hydrophobicity than an inner circumferential surface of the sheath portion.

* * * * *